(12) United States Patent
Voigt et al.

(10) Patent No.: US 12,360,428 B2
(45) Date of Patent: Jul. 15, 2025

(54) MELANIN-PEPTIDE-BASED PHOTONIC MATERIALS

(71) Applicant: Massachusetts Institute of Technology, Cambridge, MA (US)

(72) Inventors: Christopher A. Voigt, Cambridge, MA (US); Di Sheng Lee, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 572 days.

(21) Appl. No.: 17/228,637

(22) Filed: Apr. 12, 2021

(65) Prior Publication Data

US 2021/0318587 A1 Oct. 14, 2021

Related U.S. Application Data

(60) Provisional application No. 63/009,430, filed on Apr. 13, 2020.

(51) Int. Cl.
| | | |
|---|---|---|
| *G02F 1/167* | (2019.01) | |
| *C07K 7/06* | (2006.01) | |
| *C09B 61/00* | (2006.01) | |
| *G02F 1/1676* | (2019.01) | |
| *G02F 1/1675* | (2019.01) | |

(52) U.S. Cl.
CPC .............. *G02F 1/167* (2013.01); *C07K 7/06* (2013.01); *C09B 61/00* (2013.01); *G02F 1/1676* (2019.01); *G02F 2001/1678* (2013.01); *G02F 2202/02* (2013.01)

(58) Field of Classification Search
CPC .................. G02F 1/167; G02F 1/1676; G02F 2001/1678; G02F 2202/02; C07K 14/005; C07K 7/06; C07K 7/08; C07K 14/425; C07K 14/76; C07K 5/0812; C07K 5/0815; C07K 5/0819; A61Q 19/00; A61Q 19/001; A61Q 19/02; A61Q 19/04; A61Q 19/10; A61Q 5/00; A61Q 5/02
See application file for complete search history.

(56) References Cited

U.S. PATENT DOCUMENTS

| | | | |
|---|---|---|---|
| 2008/0113031 A1 | 5/2008 | Moodley et al. | |
| 2013/0115457 A1 | 5/2013 | Haynie et al. | |
| 2013/0243693 A1 | 9/2013 | Omenetto et al. | |
| 2014/0072613 A1* | 3/2014 | Lander ............... | A61K 38/1709 514/8.9 |
| 2018/0244725 A1* | 8/2018 | Wallace ................. | C07K 7/08 |

(Continued)

FOREIGN PATENT DOCUMENTS

KR 20150071967 * 6/2015 ............. A61Q 19/00

OTHER PUBLICATIONS

Xiao et al., "Elucidation of the hierarchical structure of natural eumelanin" J. R. Soc. Interface. 15: 20180045, Feb. 13, 2018 (Feb. 13, 2018).

(Continued)

*Primary Examiner* — Brandi N Thomas
(74) *Attorney, Agent, or Firm* — PABST PATENT GROUP LLP

(57) ABSTRACT

A colored composition having a self-assembly of a plurality of a peptide and melanin, and methods of producing and using the colored composition are described.

19 Claims, 20 Drawing Sheets

Specification includes a Sequence Listing.

(56) References Cited

U.S. PATENT DOCUMENTS

2018/0360995 A1 12/2018 Bancel et al.

OTHER PUBLICATIONS

International Search Report issued on Sep. 29, 2021, in co-pending PCT Application No. PCT/US2021/026922.
Written Opinion of the International Searching Authority issued on Sep. 29, 2021, in co-pending PCT Application No. PCT/US2021/026922.

* cited by examiner

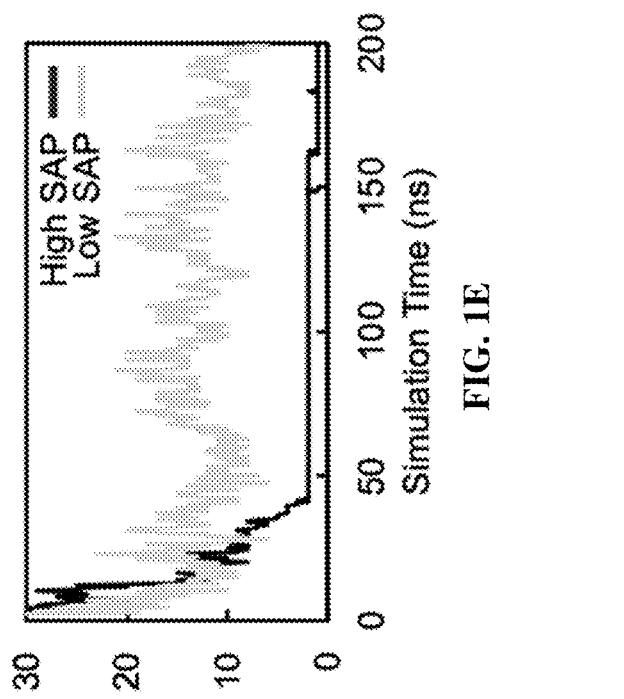
FIG. 1D
FIG. 1E
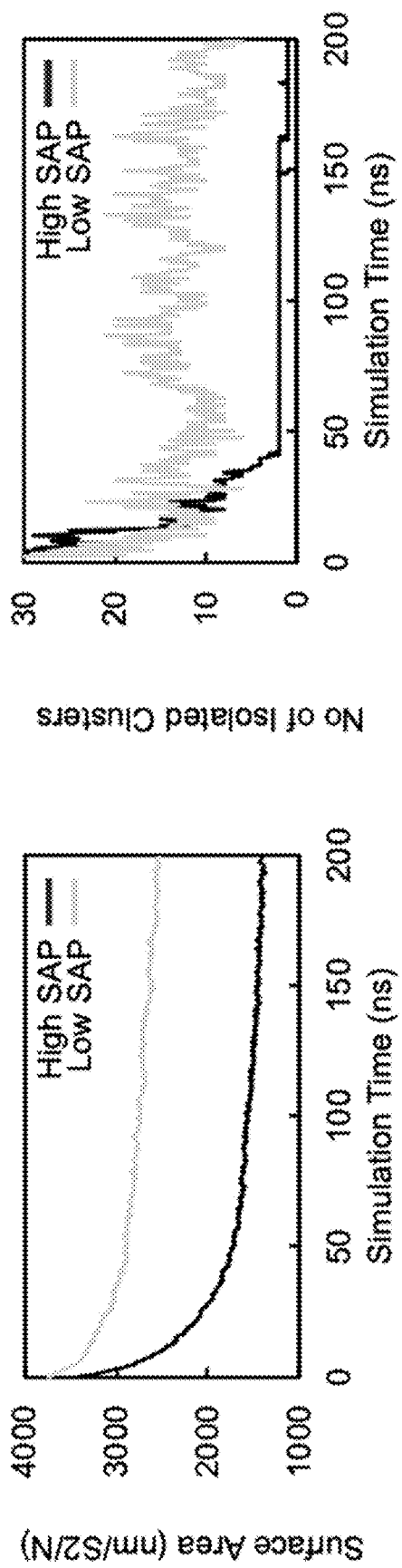
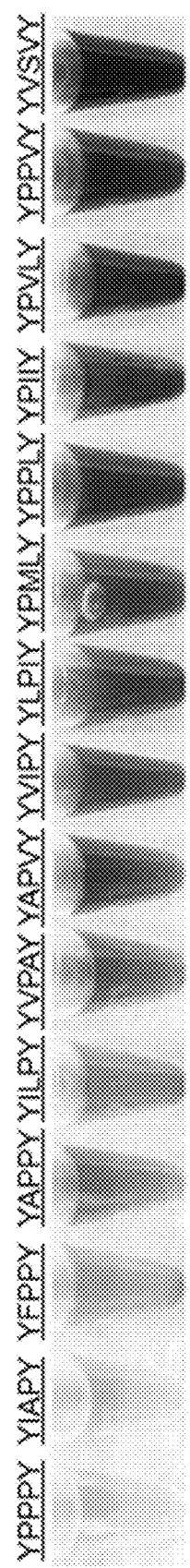
FIG. 2A

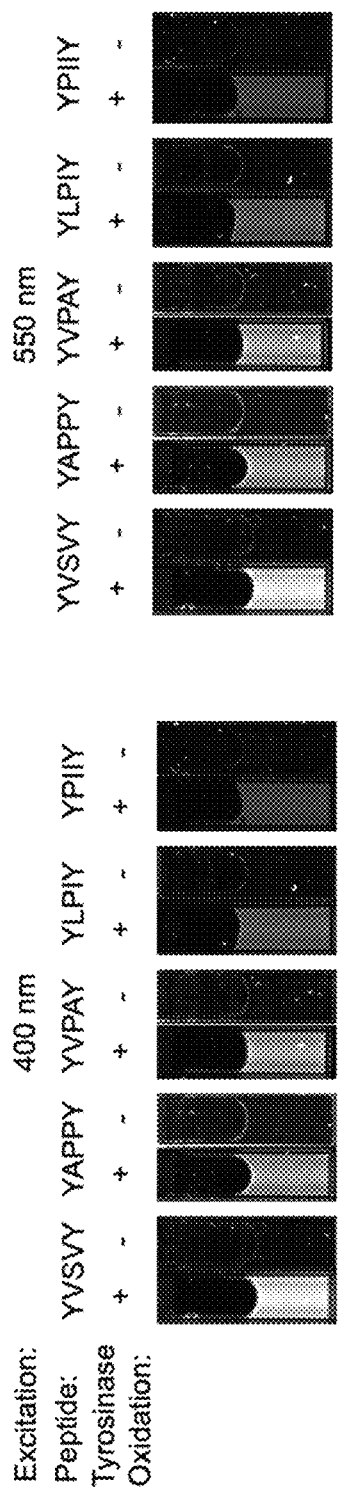
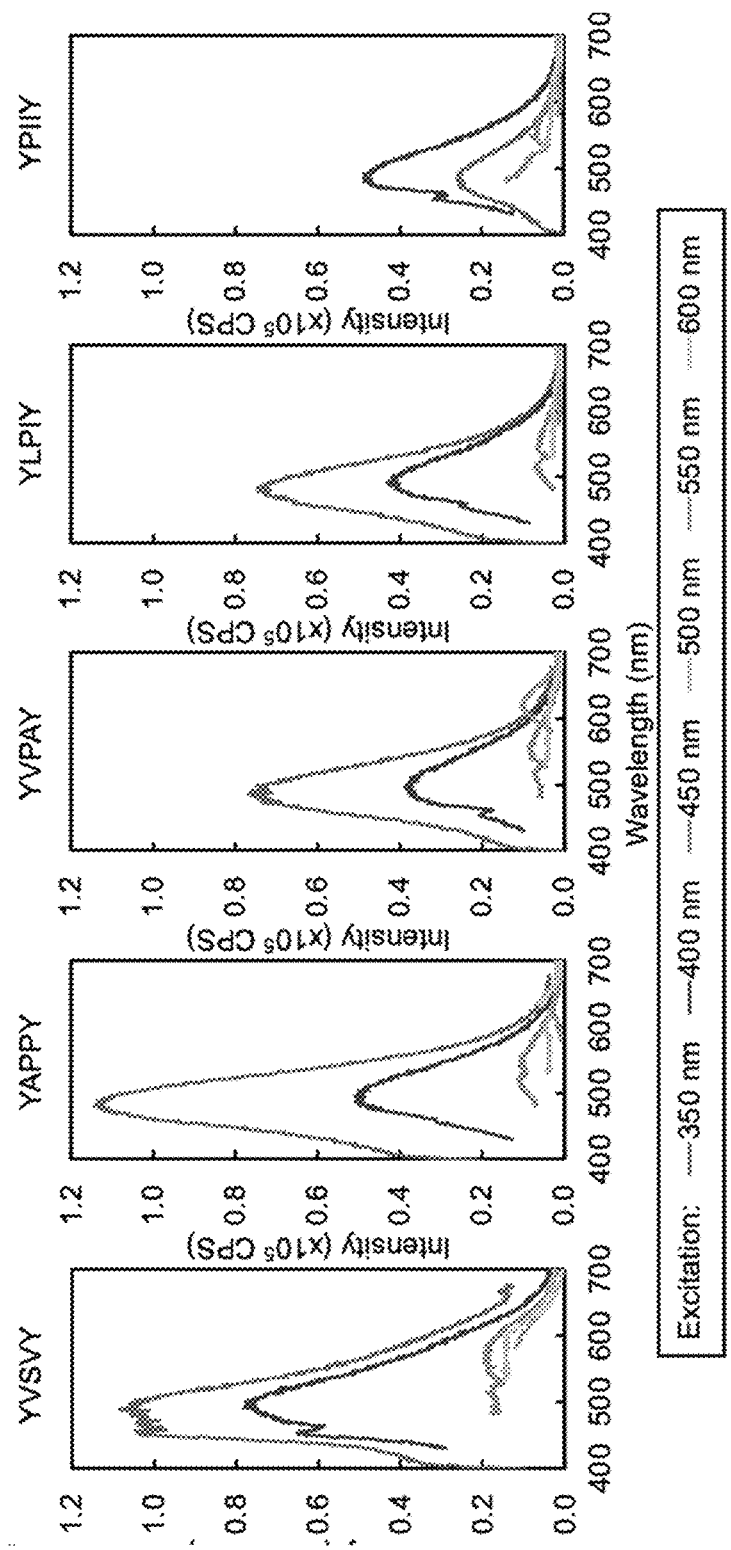
FIG. 3A
FIG. 3B

| 1-50 | 51-100 | 101-150 | 151-200 | 201-250 | 251-300 | 301-350 | 351-400 |
|---|---|---|---|---|---|---|---|
| 'GLY-GLY' | 'PHE-CYS' | 'PRO-TRP' | 'ILE-ILE' | 'GLY-ASP' | 'LYS-GLN' | 'ALA-ASN' | 'LYS-CYS' |
| 'MET-GLY' | 'GLY-TYR' | 'SER-GLY' | 'LEU-ILE' | 'GLU-ALA' | 'ARG-MET' | 'ALA-GLN' | 'LYS-VAL' |
| 'GLY-MET' | 'TRP-MET' | 'ALA-SER' | 'LEU-LEU' | 'ALA-GLU' | 'MET-ARG' | 'GLN-ALA' | 'TYR-LYS' |
| 'PHE-MET' | 'MET-HIS' | 'GLY-SER' | 'ILE-PRO' | 'ALA-ASP' | 'ARG-ALA' | 'TRP-ASN' | 'LYS-TYR' |
| 'VAL-GLY' | 'HIS-LEU' | 'SER-MET' | 'PRO-LEU' | 'ASP-ALA' | 'ALA-ARG' | 'ASP-LYS' | 'LYS-THR' |
| 'MET-MET' | 'TYR-ALA' | 'LEU-TRP' | 'LEU-PRO' | 'ASP-VAL' | 'GLY-LYS' | 'LYS-ASP' | 'LYS-SER' |
| 'GLY-VAL' | 'HIS-MET' | 'CYS-THR' | 'ALA-PRO' | 'ASP-CYS' | 'LYS-GLY' | 'TRP-GLN' | 'THR-LYS' |
| 'GLY-ILE' | 'TRP-CYS' | 'MET-THR' | 'PRO-CYS' | 'ASP-ILE' | 'ARG-VAL' | 'TYR-ASN' | 'SER-LYS' |
| 'CYS-GLY' | 'MET-TRP' | 'SER-LEU' | 'PRO-ILE' | 'CYS-ASP' | 'VAL-ARG' | 'ASN-TRP' | 'PRO-LYS' |
| 'GLY-CYS' | 'ILE-HIS' | 'THR-CYS' | 'VAL-PRO' | 'ASP-LEU' | 'CYS-ARG' | 'GLN-TRP' | 'LYS-PRO' |
| 'LEU-GLY' | 'ALA-TRP' | 'MET-SER' | 'PRO-MET' | 'GLU-VAL' | 'ARG-LEU' | 'TYR-GLN' | 'TRP-SER' |
| 'MET-CYS' | 'PHE-THR' | 'LEU-THR' | 'PRO-VAL' | 'VAL-GLU' | 'LEU-ARG' | 'ASN-TYR' | 'THR-HIS' |
| 'MET-ALA' | 'GLY-HIS' | 'THR-VAL' | 'PRO-PRO' | 'LEU-ASP' | 'ILE-ARG' | 'GLN-TYR' | 'SER-HIS' |
| 'ILE-GLY' | 'TRP-ALA' | 'THR-ALA' | 'GLN-ARG' | 'ILE-ASP' | 'ARG-CYS' | 'HIS-GLN' | 'HIS-THR' |
| 'GLY-LEU' | 'THR-PHE' | 'PRO-PHE' | 'LYS-LYS' | 'VAL-ASP' | 'ARG-ILE' | 'HIS-ASN' | 'HIS-SER' |
| 'MET-VAL' | 'SER-PHE' | 'PRO-TYR' | 'ARG-GLN' | 'GLU-PRO' | 'ARG-PHE' | 'ASN-HIS' | 'TRP-THR' |
| 'VAL-MET' | 'THR-TRP' | 'VAL-SER' | 'ASN-ARG' | 'PRO-GLU' | 'PHE-ARG' | 'GLN-HIS' | 'TYR-TRP' |
| 'ALA-ILE' | 'SER-TRP' | 'LEU-SER' | 'ARG-ASN' | 'PRO-ASP' | 'ASP-ARG' | 'HIS-HIS' | 'HIS-ALA' |
| 'ALA-LEU' | 'HIS-CYS' | 'THR-ILE' | 'LYS-ARG' | 'ASP-PRO' | 'ARG-ASP' | 'HIS-TRP' | 'ALA-HIS' |
| 'ALA-MET' | 'HIS-VAL' | 'ILE-TYR' | 'ARG-LYS' | 'SER-GLU' | 'LYS-GLU' | 'PHE-HIS' | 'PHE-SER' |
| 'ILE-MET' | 'TYR-THR' | 'CYS-TYR' | 'ARG-ARG' | 'THR-ASP' | 'GLU-LYS' | 'HIS-PHE' | 'TYR-TYR' |
| 'MET-LEU' | 'CYS-HIS' | 'LEU-TYR' | 'GLU-GLU' | 'ASP-THR' | 'GLN-GLY' | 'TRP-HIS' | 'TYR-PHE' |
| 'CYS-MET' | 'TYR-SER' | 'VAL-TYR' | 'GLU-ASP' | 'ASP-SER' | 'ASN-GLY' | 'LYS-TRP' | 'TRP-GLY' |
| 'CYS-LEU' | 'SER-TYR' | 'PHE-PRO' | 'ASP-GLU' | 'SER-ASP' | 'GLY-ASN' | 'HIS-LYS' | 'GLN-THR' |
| 'LEU-ALA' | 'SER-SER' | 'TYR-PRO' | 'ASP-ASP' | 'GLU-SER' | 'GLY-GLN' | 'TRP-LYS' | 'GLN-SER' |
| 'LEU-CYS' | 'THR-THR' | 'VAL-THR' | 'GLU-ASN' | 'GLU-THR' | 'ASN-PHE' | 'LYS-HIS' | 'THR-GLN' |
| 'LEU-MET' | 'SER-THR' | 'THR-MET' | 'ASN-GLU' | 'THR-GLU' | 'PHE-ASN' | 'SER-ARG' | 'SER-GLN' |
| 'ALA-VAL' | 'THR-SER' | 'SER-ILE' | 'GLU-GLN' | 'ASP-TYR' | 'GLN-PHE' | 'THR-ARG' | 'PHE-TRP' |
| 'VAL-ALA' | 'THR-TYR' | 'ILE-SER' | 'GLN-GLU' | 'ASP-HIS' | 'PHE-GLN' | 'ARG-THR' | 'ASN-SER' |
| 'VAL-CYS' | 'ALA-TYR' | 'THR-LEU' | 'GLN-ASP' | 'HIS-ASP' | 'MET-ASN' | 'ARG-SER' | 'THR-ASN' |
| 'ILE-ALA' | 'TRP-VAL' | 'ILE-THR' | 'ASP-GLN' | 'HIS-GLU' | 'ASN-MET' | 'TYR-ARG' | 'ASN-THR' |
| 'ILE-CYS' | 'TRP-ILE' | 'SER-VAL' | 'ASN-ASP' | 'GLU-HIS' | 'MET-GLN' | 'ARG-HIS' | 'SER-ASN' |
| 'MET-ILE' | 'TRP-LEU' | 'SER-ALA' | 'ASP-ASN' | 'ASP-TRP' | 'GLN-MET' | 'HIS-ARG' | 'HIS-GLY' |
| 'CYS-CYS' | 'TRP-PRO' | 'THR-PRO' | 'GLU-GLY' | 'TRP-ASP' | 'ASN-CYS' | 'ARG-TYR' | 'TRP-TYR' |
| 'ALA-ALA' | 'TYR-CYS' | 'PRO-THR' | 'GLY-GLU' | 'GLU-TRP' | 'CYS-ASN' | 'ARG-TRP' | 'TYR-HIS' |
| 'TYR-LEU' | 'ILE-TRP' | 'SER-PRO' | 'ASP-GLY' | 'TYR-ASP' | 'LEU-ASN' | 'TRP-ARG' | 'HIS-TYR' |
| 'CYS-ALA' | 'VAL-TRP' | 'PRO-SER' | 'GLU-MET' | 'TYR-GLU' | 'ASN-ILE' | 'PHE-LYS' | 'TRP-TRP' |
| 'ALA-CYS' | 'HIS-ILE' | 'PRO-ALA' | 'MET-GLU' | 'GLU-TYR' | 'GLN-ILE' | 'LYS-PHE' | 'TRP-PHE' |
| 'ALA-GLY' | 'VAL-HIS' | 'CYS-PRO' | 'GLU-PHE' | 'TRP-GLU' | 'VAL-ASN' | 'MET-LYS' | 'PHE-TYR' |
| 'GLY-ALA' | 'CYS-TRP' | 'VAL-LEU' | 'PHE-GLU' | 'ARG-GLU' | 'ILE-ASN' | 'LYS-MET' | 'ALA-PHE' |
| 'PHE-VAL' | 'LEU-HIS' | 'VAL-ILE' | 'ASP-PHE' | 'GLU-ARG' | 'ASN-LEU' | 'ARG-PRO' | 'PHE-ALA' |
| 'ILE-PHE' | 'HIS-PRO' | 'VAL-VAL' | 'PHE-ASP' | 'GLN-GLN' | 'LEU-GLN' | 'PRO-ARG' | 'TYR-GLY' |
| 'PHE-ILE' | 'TYR-ILE' | 'CYS-VAL' | 'MET-ASP' | 'GLN-ASN' | 'ASN-VAL' | 'LYS-ALA' | 'GLY-TRP' |
| 'LEU-PHE' | 'TYR-VAL' | 'PRO-GLY' | 'ILE-GLU' | 'ASN-GLN' | 'GLN-CYS' | 'ALA-LYS' | 'PHE-PHE' |
| 'MET-PHE' | 'GLY-THR' | 'GLY-PRO' | 'LEU-GLU' | 'ASN-ASN' | 'CYS-GLN' | 'ILE-LYS' | 'GLY-PHE' |
| 'TYR-MET' | 'ALA-THR' | 'ILE-LEU' | 'GLU-LEU' | 'LYS-ASN' | 'VAL-GLN' | 'CYS-LYS' | 'PHE-GLY' |
| 'MET-TYR' | 'PRO-HIS' | 'CYS-ILE' | 'GLU-ILE' | 'ASN-LYS' | 'GLN-LEU' | 'LEU-LYS' | 'PRO-GLN' |
| 'CYS-PHE' | 'THR-GLY' | 'LEU-VAL' | 'CYS-GLU' | 'GLN-LYS' | 'ILE-GLN' | 'LYS-LEU' | 'GLN-PRO' |
| 'VAL-PHE' | 'CYS-SER' | 'ILE-VAL' | 'GLU-CYS' | 'ARG-GLY' | 'GLN-VAL' | 'LYS-ILE' | 'PRO-ASN' |
| 'PHE-LEU' | 'SER-CYS' | 'MET-PRO' | 'ASP-MET' | 'GLY-ARG' | 'ASN-ALA' | 'VAL-LYS' | 'ASN-PRO' |

FIG. 6

MELANIN-PEPTIDE-BASED PHOTONIC MATERIALS

CLAIM OF PRIORITY

This application claims priority to U.S. Provisional Application No. 63/009,430, filed Apr. 13, 2020, which is incorporated by reference in its entirety.

FEDERALLY SPONSORED RESEARCH OR DEVELOPMENT

This invention was made with Government support under Grant No. HR0011-15-C-0084 awarded by the Defense Advanced Research Projects Agency (DARPA). The Government has certain rights in the invention.

FIELD OF THE INVENTION

The invention relates to melanin-peptide-based photonic materials.

BACKGROUND

Current state-of-the-art nanomaterials with unique optical and electronic properties originating from quantum confinement rely heavily on the use of rare-earth metals and inorganic materials. The extraction of these rare-earth metals is labor-intensive, expensive and environmentally damaging. Moreover, a critical bottleneck of existing nanomaterials is their difficulties to scale up to the macroscale, which is required for real-world technological applications.

SUMMARY

In one aspect, a colored composition can include a self-assembly of a plurality of a peptide and melanin. The peptide can include a tyrosine. The melanin can have a color defined by the self-assembly of the plurality of the peptide. The colored composition can be blue, green, yellow, orange, or red.

In certain circumstances, the peptide can be a pentapeptide. In certain circumstances, the peptide can have an N-terminal tyrosine and a C-terminal tyrosine. In certain circumstances, the peptide can have a packing sequence. In certain circumstances, the packing sequence can have three amino acids. In certain circumstances, the packing sequence can contain valine, isoleucine, proline, or combinations thereof.

In certain circumstances, the self-assembly of the plurality of the peptide can have a 3D, 2D, 1D, or 0D morphology. In certain circumstances, the 3D morphology can be a globular structure. In certain circumstances, the 2D morphology can be a sheet-like structure. In certain circumstances, the 1D morphology can be a fiber-like structure. In certain circumstances, the 0D morphology can be a quantum dot-like structure.

In certain circumstances, the peptide can have a low self-assembly potential (SAP). In certain circumstances, the peptide can have a high self-assembly potential (SAP).

In certain circumstances, the self-assembly can have a long-range order arrangement. In certain circumstances, the self-assembly can have a short-range order arrangement.

In certain circumstances, the colored composition can include a second peptide. The second peptide can include a tyrosine.

In certain circumstances, the peptide and the second peptide can be different peptides. In certain circumstances, the self-assembly can have a 3D, 2D, 1D, or 0D morphology. In certain circumstances, the self-assembly can have the same morphology. In certain circumstances, the self-assembly can have different morphology. In certain circumstances, the colored composition can be iridescent.

In another aspect, a method of producing a structural color can include selecting a sequence of a peptide including a tyrosine, permitting self-assembly of a plurality of the peptides, and oxidizing the tyrosine to form a melanin.

In another aspect, a method of producing a specular reflection structure can include selecting a first sequence of a peptide including a tyrosine, permitting self-assembly of a plurality of the peptides of the first sequence, selecting a second sequence of a peptide including a tyrosine, permitting self-assembly of a plurality of the peptides of the second sequence, combining the two self-assemblies, and oxidizing the tyrosine to form a melanin. The first sequence and the second sequence can be different sequences.

In another aspect, a colored device can include a colored composition including a self-assembly of a plurality of a peptide and melanin. The peptide can include a tyrosine.

In certain embodiments, the device can include a first electrode, a second electrode and the colored composition between the first electrode and the second electrode.

Other aspects, embodiments, and features will be apparent from the following description, the drawings, and the claims.

BRIEF DESCRIPTION OF DRAWINGS

FIGS. 1A-1E depict molecular dynamics simulation of 8,000 peptides to mine quantum-confined peptide assemblies. FIG. 1A shows each pentapeptide is made up of a three-amino-acid-long packing sequence and two tyrosine residues. The packing sequence has a structural role that dictates self-assembly potential (SAP), while tyrosine has a functional role and is placed at the end for easy tyrosinase enzyme access to oxidize tyrosine residues into conjugated system. FIG. 1B shows that high and low SAP peptide assemblies have different size and compacity: high SAP structures are small and compact, while low SAP structure are loose and exposed. FIG. 1C depicts the simulation results of all 8,000 peptide SAP were plotted in a 2-dimensional heatmap. The results were clustered using hierarchical clustering to establish sequence-structure relationship. The y-axis dendrogram labels are provided in the table shown in FIG. 6. FIGS. 1D-1E show real-time structural analysis of high and low SAP structures in terms of total exposed surface area and number of isolated clusters versus time. The total exposed surface area and number of isolated clusters of high SAP structure decreased more significantly with time compared to low SAP structure.

FIGS. 2A-2B depict the production and characterization of quantum-confined enzymatically modified peptide assemblies. FIG. 2A shows post-production enzymatical modification turned colorless peptide solutions into yellow, orange, red and dark red colored solutions respectively after 24 hours of oxidation under ambient conditions. All subpanels reflect representative data from experiments repeated three times on different days (SEQ ID NOs. 23 and 1-14, respectively, in order of appearance). FIG. 2B shows enzymatically modified peptides with different sequences were observed to form a variety of quantum-confined structures with sizes that range from a few hundred nanometers to a few microns and different 1D, 2D, 3D morphologies. All subpanels reflect representative data from experiments repeated three times on different days. (SEQ ID NOs. 14, 3, 2, 8, 13, and 11, respectively, in order of appearance).

FIGS. 3A-3C depict photoluminescence (PL) properties of enzymatically modified quantum-confined peptide assemblies. FIG. 3A shows different PL emission intensities were observed in non-modified and enzymatically modified peptide assemblies. PL emission was measured at two different excitation wavelengths: 400 nm and 550 nm respectively (SEQ ID NOs. 14, 3, 5, 8, and 11, respectively, in order of appearance). FIG. 3B shows the PL spectra of enzymatically modified peptide assemblies were obtained using spectrofluorometer at a series of excitation wavelengths from 350 nm to 600 nm (SEQ ID NOs. 14, 3, 5, 8, and 11, respectively, in order of appearance). FIG. 3C shows fluorescence characterization of enzymatically modified peptide assemblies using fluorescence microscope at a series of excitation wavelengths from 395 nm to 560 nm. All subpanels reflect representative data from experiments repeated three times on different days. (SEQ ID NOs. 14, 8, 5, 11, and 3, respectively, in order of appearance).

FIG. 4A shows colorful structural pigments ranging from red, orange, yellow, green to grey-blue were formed by selecting peptide sequences with different SAP (SEQ ID NOs. 5, 11, 8, 14, 3, 15-19, 5, 10, 20, 23, 24, and 21, respectively, in order of appearance). FIG. 4B shows the UV-Vis spectra of various structural pigments obtained using UV-Vis spectroscopy.

FIG. 5A shows Martini coarse-grained force field were performed 8,000 times for each peptide. FIG. 5B shows SAP of peptides with packing sequence of 3, 6, 9 and 12 amino acids. The data represent the average of five independent simulations. The error bars represent the standard deviation across the five independent simulations. FIG. 5C shows peptide sequences with varying SAP that were selected for experiments (SEQ ID NOs. 8, 13, 4, 16, 10, 9, 3, 6, 17, 12, 5, 21, 14, 11, 1-2, and 18-20, respectively, in order of appearance).

FIG. 6 depicts the Y-axis of FIG. 1C heatmap dendrogram. The first and second amino acid of the packing sequence is arranged in order. 'GLY-GLY' is the first amino acid pair at the top of the dendrogram, while 'ASN-PRO' is the last amino acid pair at the bottom of the dendrogram.

FIG. 13A shows a library of potential 1D morphologies of various self-assemblies of peptide sequences (SEQ ID NOs. 78-82, 16, 83-102, 11, 103-108, 5, and 105, respectively, in order of appearance). FIG. 13B shows a library of potential 2D morphologies having a "C"- or "L"-like shapes of various self-assemblies of peptide sequences (SEQ ID NOs. 25-34, 3, and 35-62, respectively, in order of appearance). FIG. 13C shows a library of potential 2D morphologies having a "Y"-, "U"-, "V"-, "h"-, or "F"-like shapes of various self-assemblies of peptide sequences (SEQ ID NOs. 63-77, 114-123, and 132-137, respectively, in order of appearance). FIG. 13D shows a library of potential 2D morphologies having various shapes such as a "O"-, "4" or "7"-like shapes of various self-assemblies of peptide sequences (SEQ ID NOs. 138-160, 110-113, and 124-131, respectively, in order of appearance).

DETAILED DESCRIPTION

A colored composition having a self-assembly of a plurality of a peptide and melanin, and methods of producing and using the colored composition are described. The peptide includes a tyrosine. The melanin has a color defined by the self-assembly of the plurality of the peptide. The colored composition can be blue, green, yellow, orange, red, or colors in between.

Figure 1A:
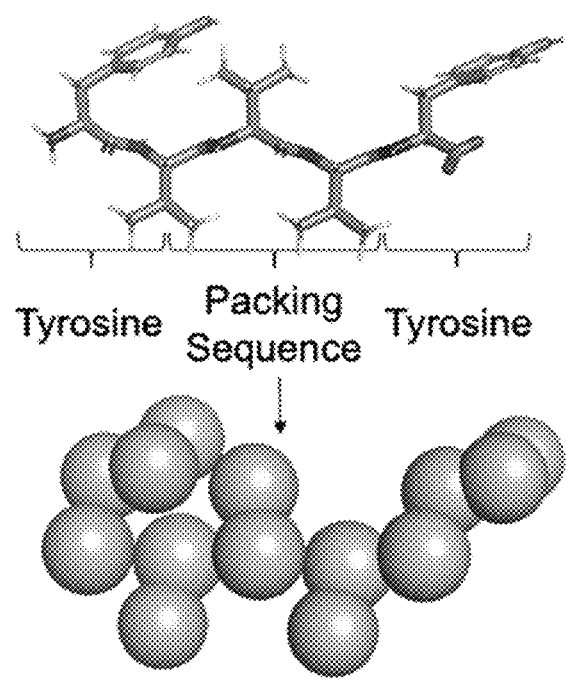

Some of the peptides described herein are pentapeptides. The pentapeptides have a three-amino-acid-long packing sequence and a tyrosine residue at each end of the peptide (FIG. 1A). The packing sequence can dictate the size, compacity, and morphology of the peptide assemblies, while the tyrosine residue at each end of the pentapeptide can allow for post-production enzymatic modification. The amino acids of the packing sequence can be any one of the naturally occurring amino acids and be in any combination, depending on the size, compacity and/or morphology a skilled artisan would want to achieve. For example, the packing sequence can contain valine, isoleucine, proline, or combinations thereof. In another example, the packing sequence may contain hydrophobic and short polar amino acid residues. In another example, the packing sequence may contain charged and long polar amino acid residues.

Figure 5A:
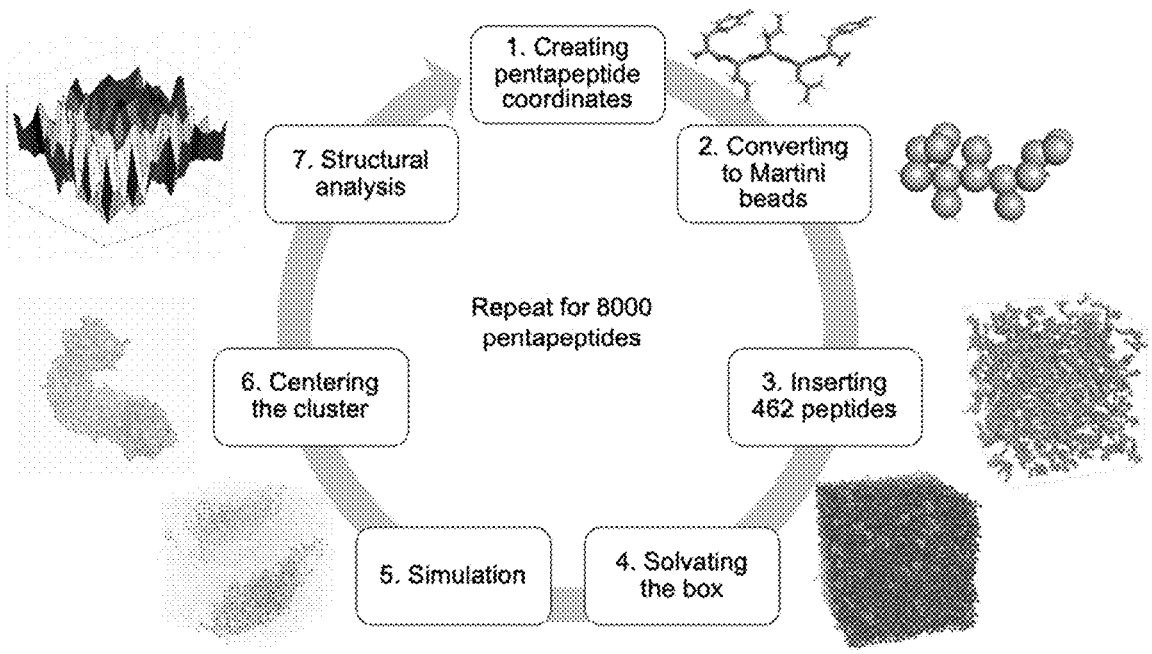
FIGS. 5A-5C depict molecular dynamics (MD) simulation pipeline to mine peptides with different SAP.
Figure 5B:
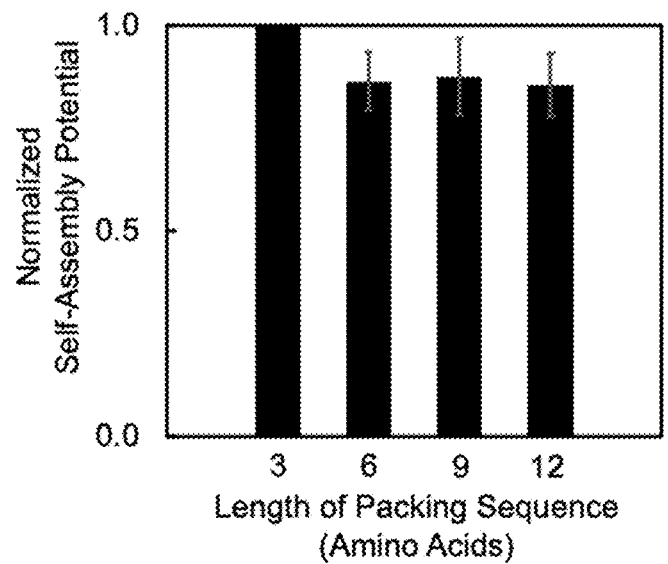

The number of amino acids present in the packing sequence can vary, depending on the size, compacity and/or morphology a skilled artisan would want to achieve. For example, longer packing sequence may compromise self-assembly potential, precluding quantum-confined peptide assemblies from forming (FIG. 5B). In certain embodiments, the packing sequence is longer that three amino acids so as to confer more polymer-like properties in the peptide. In a preferred embodiment, the packing sequence is three amino acids long.

Figure 4A:
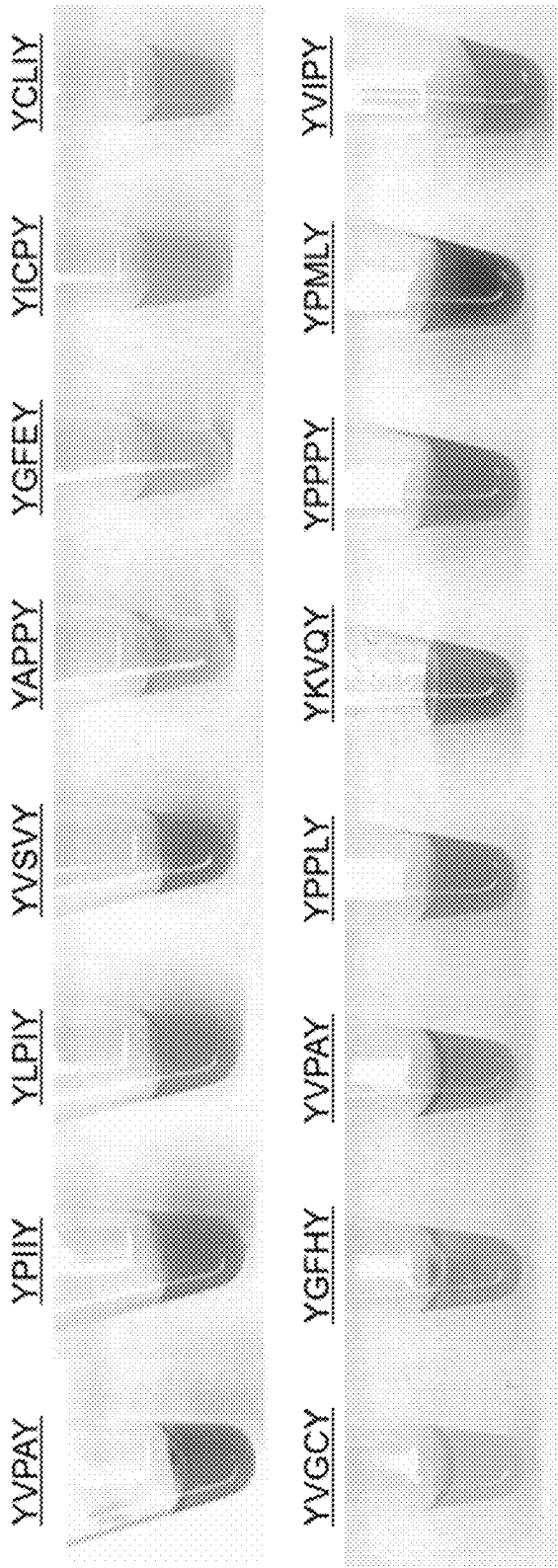
FIGS. 4A-4B depict formation of colorful amorphous structural pigments from enzymatically modified peptide assemblies.
Figure 4B:
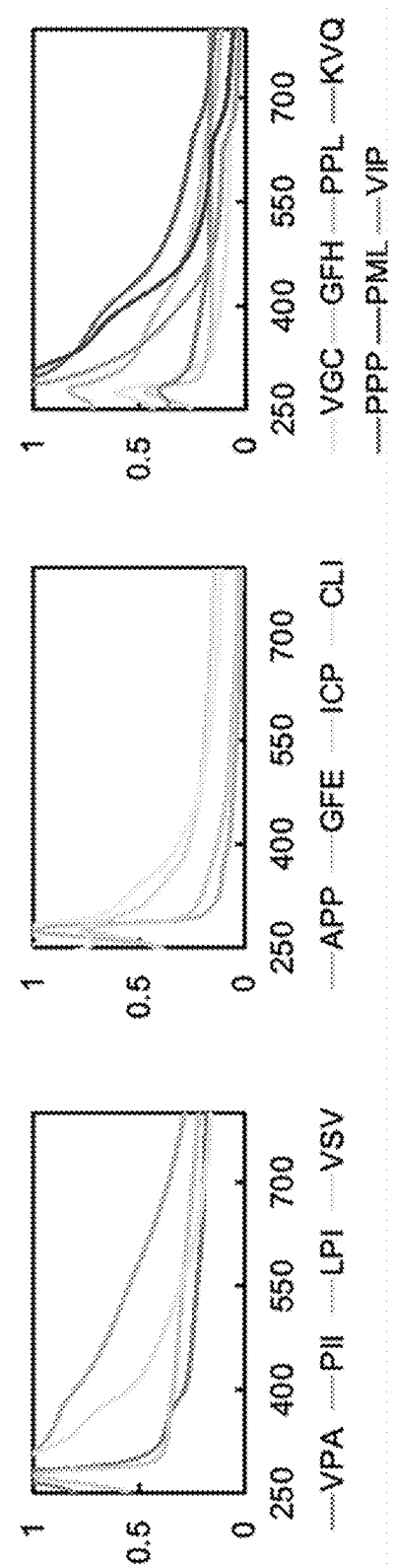

The selection of amino acids of the packing sequence varies depending on the size, compacity and/or morphology a skilled artisan would want to achieve. For example, a small or a large size would want to be achieved. A small size can be a structure of less than 500 nm. A large size can be a structure of more than 500 nm. In another example, a compact or a loose structure would want to be achieved. Similarly, a high or low self-assembly potential (SAP) of the plurality of the peptide would want to be achieved. SAP can be calculated from the ratio of initial and final solvent-accessible surface area. The peptide can have a low SAP or high SAP. A low SAP is a peptide with a SAP of less than 6.0. A high SAP is a peptide with a SAP of more than 6.0. FIGS. 4A-4B show colorful amorphous structural pigments from enzymatically modified peptide assemblies with different SAP.

The amino acids of the packing sequence can contribute to the self-assembly of the plurality of a peptide. The self-assembly of the plurality of the peptide can have a 3D, 2D, 1D, or 0D morphology. The 3D morphology can be a globular structure or a globular-like structure or have a globular-like appearance. The 2D morphology can be a sheet-like structure or a sheet-like structure. The 2D morphology can have a "C", "L", "Y", "X", "O", "F", "U", "h", "V", "4", "7", "P"-like appearance/shape. The 1D morphology can be fiber-like structure. The 0D morphology is a quantum dot-like structure. See, FIGS. 13A-13D.

The self-assembly of the plurality of the peptide can have a long-range order arrangement. The self-assembly of the plurality of the peptide can have a short-range order arrangement. In certain embodiments, the self-assembly of the plurality of the peptide can have a long-range order arrangement and a short-range order arrangement. In certain embodiments, the self-assembly of the plurality of the peptide can have a short-range order arrangement and not a long-range order arrangement. For example, high ion concentration used during the peptide self-assembly process can facilitate the breakdown of long-range order arrangement. High ion concentration may be doubling the ion concentration. For example, an ion concentration of 15 mM, 20 mM, 25 mM, 30 mM.

Melanin is well known to be capable of absorbing incoherent scattering light, helping to enhance color saturation and contrast. Melanin is made up of indolic monomers derived from the enzymatic oxidation of tyrosine. Those indolic monomers include monomer 5,6-dihydroyindole (DHI), 5,6-dihydroxyindole-2-carboxylic acid (DHICA), as well as other redox forms, and these monomers are randomly cross-linked into conjugated homo- or heteropolymers stabilized by aromatic π-interactions. This extended, conjugated system of melanin endows melanin with a broadband absorption spectrum with near unity nonradiative conversion of absorbed photon energy, making it black and crucial to absorbing incoherent scattering.

Melanin or melanin-like material can be formed by enzymatically modifying the peptide self-assemblies. For example, tyrosinase (an enzyme) can be used to oxidized the tyrosine present in the peptides. In a preferred embodiment, melanin can be formed through oxidative coupling of the tyrosine residues present in the self-assemblies of the peptides described herein. The melanin formed in the self-assemblies can have a controlled length, which can impact color. The peptide solutions may turn from colorless to colored after enzymatic modification with tyrosinase. The enzymatically modified peptide assemblies can result in a structural color. The color arises from packing of melanin, i.e. different conformations, based quantum confinement effect and coherent scattering. For example, the color may arise from limiting or enhancing the ability to form melanin with long or short conjugation lengths of the peptide self-assemblies. The resulting colors can be across the whole visible spectrum, for example blue, green, yellow, orange, red, and colors in between. When referring to the color blue, green, yellow, orange, and red, it is to be understood that said colors include a spectrum of each color. For example, when referring to blue it is meant to include light blue, dark blue, royal blue, navy blue, aquamarine, teal, teal blue, etc.

Structural colors have numerous advantages over conventional pigments or coloring agents that are toxic, unstable, and tend to fade. In order to exploit structural color for photonic applications, it is important that the structural color does not suffer from angle dependence. This can be achievable through non-crystalline, amorphous structural colors which are also known as photonic glasses. The enzymatically modified peptide assemblies described herein belong to this class of material. Accordingly, the enzymatically modified peptide assemblies described herein have multiple advantages over conventional pigments. For example, they not toxic as their components, melanin and peptides, are biodegradable. In contrast, non-structural pigments can be toxic, particularly inorganic-based pigments which are hazardous. Further, they have a charge that is easier to control, as the particle charge depends on their corresponding peptide sequence, unlike non-structural pigments which require the use of charge control agents in electrophoretic media. Another advantage of the enzymatically modified peptide assemblies described herein is that they do not require an optically absorbing dye, as melanin absorbs scattered light, contrary to non-structural pigments which require an external absorbing dye in fluid to absorb scattered light. Yet another of the enzymatically modified peptide assemblies described herein is that they can last for decades; color-imparting melanosomes were found in fossils. In contrast, non-structural pigments are susceptible to UV and photo-degradation which makes them last, at most, for years.

The enzymatically modified peptide assemblies have superior photothermal stability and minimal photobleaching. For example, the photoluminescence of the enzymatically modified peptide assemblies remains intact after heated at 200° C. for 2 hours. Further, the of the enzymatically modified peptide assemblies remains intact after 1 hour of UV radiation/exposure.

A method of producing a structural color is also described. The method of producing a structural color can be performed by selecting a sequence of a peptide including a tyrosine, permitting self-assembly of a plurality of the peptides, and oxidizing the tyrosine to form a melanin.

Permitting self-assembly of a plurality of the peptides can be achieved by allowing the plurality of peptides to sit undisturbed for a period from 2 hours to 2 weeks. For example, a period of 2 hours, 4 hours, 8 hours, 12 hours, 1 day, 3 days, 5 days, 7 days, 10 days, 12 days, and 14 days.

Oxidizing the tyrosine present in the peptides forms melanin. This step or process may be referred to as a post-production enzymatic modification. The use of post-production enzymatic modification under ambient conditions introduces aromatic, conjugated systems into quantum-confined peptide structures. This, in turn, allows tuning of the peptides optical and electronic properties. Tyrosinase can be used to oxidized the tyrosine present in the peptides. In some embodiments, tyrosinase enzyme, pH 7 at ambient temperature and pressure, is used to oxidize the tyrosines present in the peptides. The oxidation process takes place until a steady-state color is obtained. For example, the oxidation process may take from about 1 week to about 2 weeks, or it may take 2 weeks. After enzymatic modification with tyrosinase, the peptide solutions may turn from colorless to a color. The obtained colors are across the whole visible spectrum, for example blue, green, yellow, orange, red, and colors in between.

A method of producing a specular reflection structure is also described. The method of producing a specular reflection structure can include selecting a first sequence of a peptide including a tyrosine, permitting self-assembly of a plurality of the peptides of the first sequence, selecting a second sequence of a peptide including a tyrosine, permitting self-assembly of a plurality of the peptides of the second sequence, combining the two self-assemblies, and oxidizing the tyrosine to form a melanin.

The first sequence and the second sequence may be different sequences. In certain embodiments, two self-assemblies are combined prior to oxidizing the tyrosine to form a melanin. The two self-assemblies are combined in a 50:50 molar ratio. In alternative embodiments, the two self-assemblies are combined in a 10:90, 20:80, 30:70, 40:60, 60:40, 70:30, 80:20 or 90:10 molar ratio. In an example, the self-assembly of the plurality of the first peptide and the second self-assembly of the plurality of the second peptide have the same morphology. In another example, the self-assembly of the plurality of the first peptide and the second self-assembly of the plurality of the second peptide have different morphology. A colored composition having two self-assemblies can be iridescent or form a specular reflection structure.

The specular reflection structure can have a 3D, 2D, 1D, or 0D morphology. The specular reflection structure's morphology may be the same morphology as the morphology of the self-assemblies of the first and second peptides. The specular reflection structure's morphology may be a different morphology compared to the morphology of the self-assemblies of the first and second peptides. For example, the specular reflection structure's morphology may be an intermediate and/or distinct structure compared to the morphology of the self-assemblies of the first and second peptides. The 3D morphology can be a globular structure or a globular-like structure or have a globular-like appearance. The 2D morphology can be a sheet-like structure or a sheet-like structure. The 2D morphology can have a "C", "L", "Y", "X", "O", "F", "U", "h", "V", "4", "7", "P"-like appearance/shape. The 1D morphology can be fiber-like structure. The 0D morphology is a quantum dot-like structure.

In alternative embodiments, two peptides are combined to result in a single self-assembly. The peptides are combined in a 50:50 molar ratio. In alternative embodiments, the two self-assemblies are combined in a 10:90, 20:80, 30:70, 40:60, 60:40, 70:30, 80:20 or 90:10 molar ratio. The resultant single self-assembly is oxidized to form a melanin. A colored composition having two peptides/single self-assembly can be iridescent or form a specular reflection structure. The specular reflection structure resulting from the single self-assembly can have a 3D, 2D, 1D, or 0D morphology. The 3D morphology can be a globular structure or a globular-like structure or have a globular-like appearance. The 2D morphology can be a sheet-like structure or a sheet-like structure. The 2D morphology can have a "C", "L", "Y", "X", "O", "F", "U", "h", "V", "4", "7", "P"-like appearance/shape. The 1D morphology can be fiber-like structure. The 0D morphology is a quantum dot-like structure.

A colored device is also described. The colored device can include a colored composition including a self-assembly of a plurality of a peptide and melanin. The peptide can contain a tyrosine.

The colored device can include a first electrode, a second electrode, and the colored composition between the first electrode and the second electrode.

EXAMPLES

Most nanomaterials rely heavily on the use of expensive and environmentally damaging rare-earth metals and inorganic materials to derive their optical and electronic properties. However, through various combinatorial routes of post-translational biomolecular modifications, many naturally occurring bionanomaterials such as diatom, melanin and keratin are found to exhibit equally impressive optical and electronic properties including photo/electroluminescence, structural coloration, birefringence, iridescence, dielectric and semiconducting properties. Understanding and establishing the sequence-structure-function relationship of these post-translationally modified biomolecules would enable the production of rare-earth-free organic bionanomaterials with desired properties under ambient conditions. Here, post-production enzymatic modification is used to introduce aromatic, conjugated systems into quantum-confined peptide structures mined from computer simulations as an attempt to tune their optical and electronic properties in a bottom-up manner from the peptide sequence level. A library of 8,000 self-assembling short pentapeptides was screened and selected peptide sequences were found to self-assemble into structures that exhibit broad-spectrum photoluminescence with excellent photothermal stability that could rival those of inorganic quantum dots as well as vivid structural coloration. Moreover, their quantum-confined properties were retained as they were scaled up into the macroscale, making them very attractive as highly scalable and environmentally friendly alternatives to rare-earth-based inorganic nanomaterials for real-world optical and electronic applications.

Current state-of-the-art nanomaterials with unique optical and electronic properties originating from quantum confinement rely heavily on the use rare-earth metals and inorganic materials (Ref. 1, Ref 2). The extraction of these rare-earth metals is labor-intensive, expensive and environmentally damaging (Ref. 3, Ref. 4). Moreover, a critical bottleneck of existing nanomaterials is their difficulties to scale up to the macroscale, which is required for real-world technological applications (Ref. 5, Ref. 6).

On the other hand, Mother Nature has already invented a plethora of biologically produced nanomaterials with fascinating optical and electronic properties that are free from rare-earth metals. For example, compact nanosized diatoms possess quantum-confined properties capable of converting highly energetic photons into photosynthetically active radiation to power photosynthesis in the ocean (Ref 7). In another example, the intricate nanoarchitecture found on butterfly wing is responsible for its beautiful polarized iridescence and structural coloration (Ref. 8). Neuromelanin, one of the most overlooked molecules in modern medicine, is a self-assembled dopamine-derived complex pigment found in the substantia nigra and locus coeruleus of the brain, playing a vital role in electrical stimulation of the brain (Ref. 9). All these highly scalable, naturally occurring bionanomaterials with quantum-confined properties could serve as a good benchmark to address some if not all of nanomaterials current pressing issues.

One of the recurring themes in these biologically produced quantum materials is that they are all made up from amino acids and peptides. This is not surprising since peptide is made from a diverse library of 20 amino acids with their own unique chemical composition, which could enable a huge combinatorial set of sequence, structure and function. And this is the reason why peptides have successfully garnered chemists and nanotechnologists attentions on its potential as self-assembly building block to form nanostructures of different sizes and geometries (Ref. 10, Ref 11). Its molecular interactions, namely Van der Waals forces, covalent bond, hydrophobic interaction, and hydrogen bond represent a rich toolkit to build nano-assemblies with different properties and functions.

However, peptides by themselves have limited optical and electronic properties. To improve these properties, there are two main strategies: (1) by templating inorganic particles or (2) by introducing aromatic, conjugated systems. Past efforts have solely relied on the former strategy to derive the desired optical and electronic properties from inorganic materials and do not solve the inherent inability of peptides to display those properties (Ref. 12-14). The latter strategy, however, has limited success due to limited chemical synthetic strategies to engineer aromatic, conjugated systems into peptides (Ref. 15).

Disclosed herein, are peptides designed with the desired optical and electronic properties by using the latter aforementioned strategy to introduce aromatic, conjugated systems through enzymatic modification under ambient conditions with minimal energy usage and waste products. This is an example of post-translation modifications (PTMs) that biology relies on to extend the functionalities of bionanomaterials beyond those of their naturally occurring building blocks (Ref 16). For example, although melanin is just an enzymatically oxidized product of tyrosine amino acid, the conjugated system found in melanin has conferred it far more superior optical and electronic properties than its tyrosine building block (Ref 17-20). Its post-translationally modified conjugated system plays in a vital role in protecting fragile life forms on Earth and enables melanotic microbes and fungal species to thrive in some of the most extreme environments on our planet, including high-altitude Arctic and Antarctic regions (Ref 21, Ref 22) as well as abandoned nuclear reactor in Chernobyl (Ref. 23, Ref. 24). Moreover, cryptoendolithic black fungi *Cryomyces antarcticus* can even survive cosmic radiation in outer space and simulated Mars conditions because of its thick melanized cell walls (Ref 25-27).

As described herein, a library of 8,000 self-assembling short pentapeptides was screened to mine peptide sequences that could form quantum-confined structures with interesting optical and electronic properties. This bottom-up approach is made possible by establishing the peptide sequence-structure-function relationship through molecular dynamics simulations based on Martini coarse-grained (CG) force field. As a result, the quantum-confined properties can be tuned from the peptide sequence level through the combinatorial properties of 20 different amino acids. We found that post-enzymatical modification, the conjugated peptide assemblies exhibited broad-spectrum photoluminescence properties with excellent photothermal stability that could rival those of inorganic quantum dots as well as structural coloration that resemble those in nature without the use of any inorganic particles at all. Moreover, their quantum-confined properties were retained as these peptide nanoassemblies were extended into the macroscale, making them a highly scalable and environmentally friendly replacement for rare-earth-based inorganic nanomaterials in optical and electronic applications.

Results
Mining Quantum-Confined Peptide Assemblies Through Simulations

To produce quantum-confined peptide assemblies, we designed a pentapeptide consisting of a three-amino-acid-long packing sequence and a tyrosine residue at each end of the peptide (FIG. 1A). The packing sequence dictates the size, compacity and morphology of the peptide assemblies, while the tyrosine residue at each end of the pentapeptide allows for post-production enzymatic modification. The packing sequence is restricted to three amino acids only as longer packing sequence will confer more polymer-like properties and compromise self-assembly potential, precluding quantum-confined peptide assemblies from forming (FIG. 5B).

One of the challenges in predicting the relationship between packing sequence and self-assembly potential (SAP) is the sheer number of possible packing sequence combinations. Since there are 20 amino acids, there could theoretically be 8,000 unique packing sequences as peptide has different N- and C-terminus. To screen all 8,000 packing sequences for candidates with high self-assembly potential to form quantum-confined structures in a high-throughput manner, molecular dynamics simulation specifically Martini coarse-grained force field was performed.

Figure 1B:
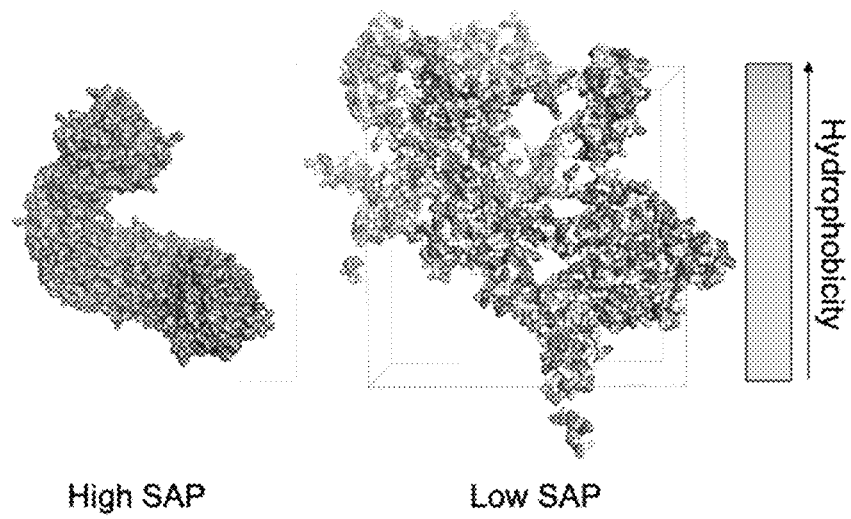
Figure 1C:
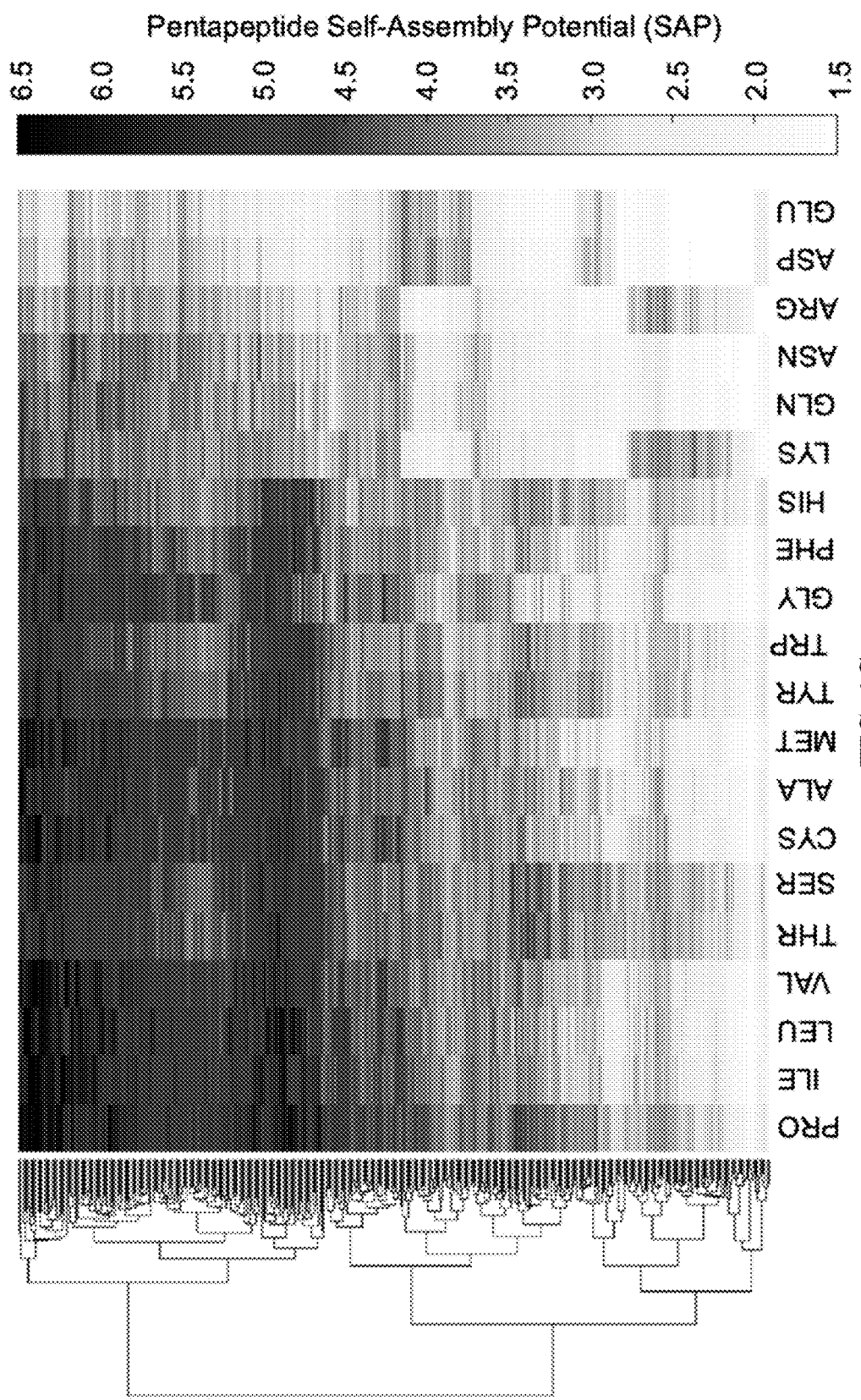

First, all 8,000 pentapeptide coordinate files were created using visual molecular dynamics (VIVID) scripting tools and converted to coarse-grained (CG) representation using Martini force field version 2.6. See FIG. 5A. Using GROMACS version 2019.2, a cubic box of 15×15×15 $nm^3$ containing 462 pentapeptides (equivalent to ~20 mg/ml) was created in standard CG water. The peptide side chains were in their prevalent charge states at neutral pH. The parameters for LJ interactions, electrostatic interactions, relative dielectric constant in standard CG water and energy minimization steps were in accordance to those used by Frederix et al. (Ref. 28). The total simulation time is 200 ns 'effective time', and the simulations were run on MIT Supercloud. SAP was calculated from the ratio of initial and final solvent-accessible surface area. A high SAP quantum-confined structure has small and compact structure, while a low SAP structure has loose structure (FIG. 1B). To perform structural analysis, GROMACS was used to track the number of clusters and their average size and align them along its principal axes. By repeating the same pipeline for all 8,000 pentapeptides, SAPs of all peptides were clustered using hierarchical clustering to establish sequence-structure relationship that could reveal which peptide sequence has potential to form quantum-confined structure. The SAPs of all 8,000 pentapeptides were plotted in FIG. 1C in the form of a heatmap. The total exposed surface area as well as number of isolated clusters of the high and low SAP peptide assemblies were plotted against time on FIGS. 1D-1E. The total exposed surface area is a measure of SAP, while the number of isolated clusters is a measure of compactness/confinement of the structure.

Figure 2B:
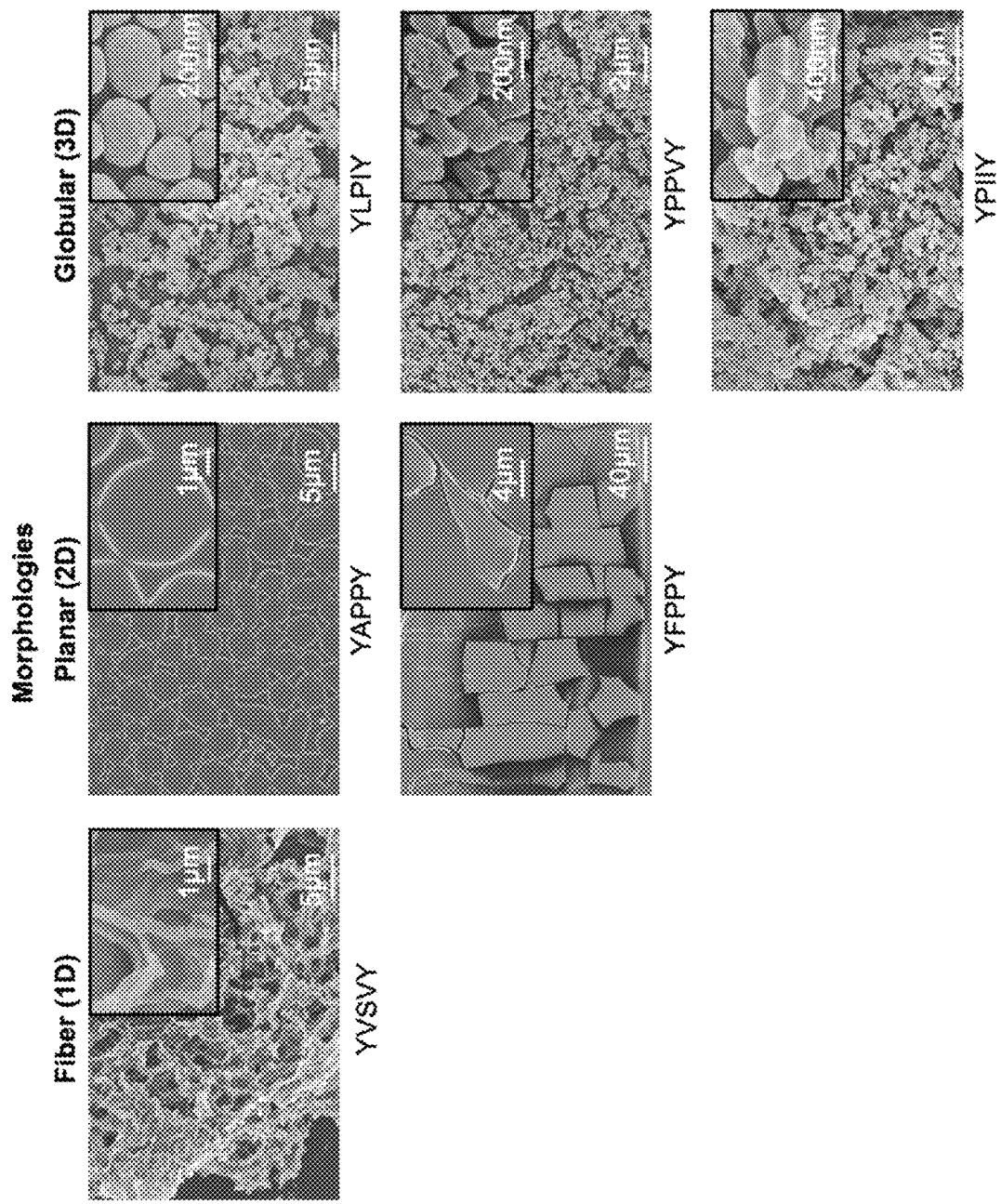
Figure 5C:
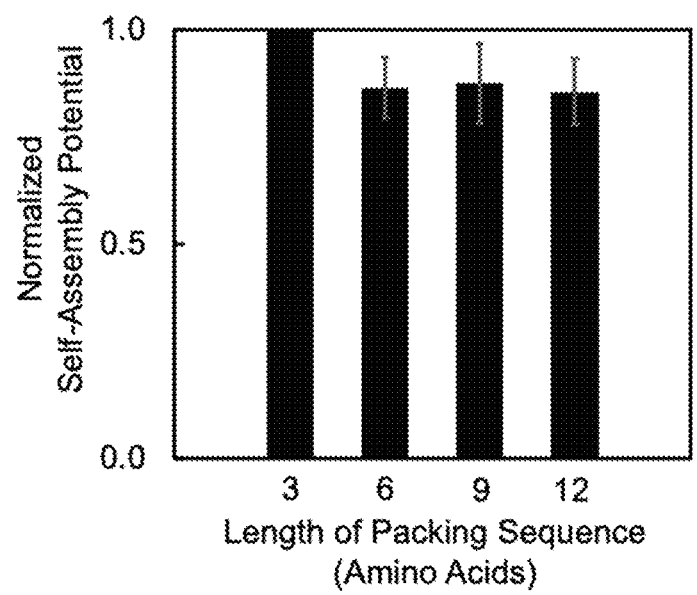

Nanomicrostructures and Quantum-Confined Properties of Enzymatically Modified Peptide Assemblies From the simulation results, peptides with medium to high SAP were chosen to produce quantum-confined structures (FIG. 5C). All peptides were dissolved in water to a final concentration of 10 mg/ml to maximize solubility. Peptide solutions were optionally heated at 80° C. for 5 minutes until the solutions turn clear and cooled to room temperature to enhance solubility. Tyrosinase was added to the peptide solution after self-assembly to a final concentration of 0.2 mg/ml to modify tyrosine into conjugated system, and the enzymatical modification process was allowed to run for 24 hours at ambient temperature and pressure. Scanning electron microscopy (SEM) was subsequently performed to characterize their nanostructures. Quantum-confined peptides were successfully produced and found to possess sizes that range from a few hundred nanometers to a few microns and morphologies that range from fiber, planar, to globular (FIGS. 2A-2B). According to previous reports, these different sizes and morphologies confer quantum-confined properties of varying degree to the nanomaterials (Ref 29), and that photoluminescence (PL) and the solution color are good indicators of these properties (Photoluminescence mechanism in graphene quantum dots: Quantum confinement effect and surface/edge state Color science of nanocrystal quantum dots for lighting and displays). ChemiDoc imager was used to visualize their PL emission, while the solution color was observed using naked eye. As expected, weak PL emissions were observed, while their solution colors remained colorless (FIG. 6), suggesting that no band gaps were formed and these peptide assemblies have limited optical and electronic properties.

To circumvent this limitation, the introduction of aromatic, conjugated system through enzymatic modification was hypothesized to be able to enhance their quantum-confined properties. As shown in FIG. 3A, post-production enzymatically modified peptide assemblies clearly showed much stronger PL emission than non-modified ones. The intensity of PL emission varies depending on the underlying peptide sequence and structure, decreasing from left to right in the order of YVSVY (SEQ ID NO. 14), YAPPY (SEQ ID NO. 3), YVPAY (SEQ ID NO. 5), YLPIY (SEQ ID NO. 8) to YPIIY (SEQ ID NO. 11).

Figure 7:
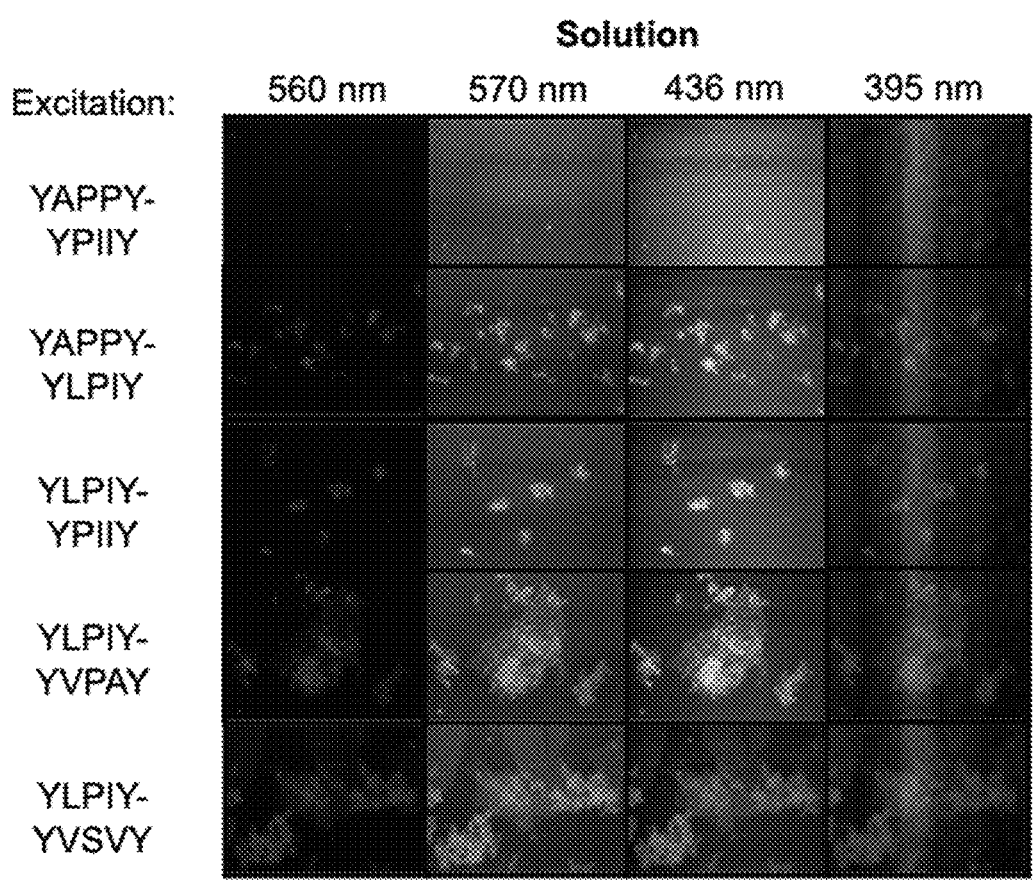
FIG. 7 depicts fluorescence characterization of hybrid enzymatically modified peptide assemblies. Two peptide sequences with different SAP were mixed to produce hybrid enzymatically modified peptide assemblies with intermediate structure and function (SEQ ID NOs. 3, 11, 3, 8, 8, 11, 8, 5, 8, and 14, respectively, in order of appearance).

Spectrofluorometer was used to quantitatively measure the PL spectrum of each peptide. See FIG. 7. Their PL spectra revealed that they have broad PL emission across the whole visible spectrum (FIG. 3B), and their PL intensities decrease in the same order from left to right. Amazingly, the solution color of these post-production enzymatically modified peptide display turned from colorless to yellow, orange and red respectively (FIG. 2B), suggesting that band gaps were successfully formed in these peptide assemblies through the introduction of aromatic, conjugated systems.

Figure 3C:
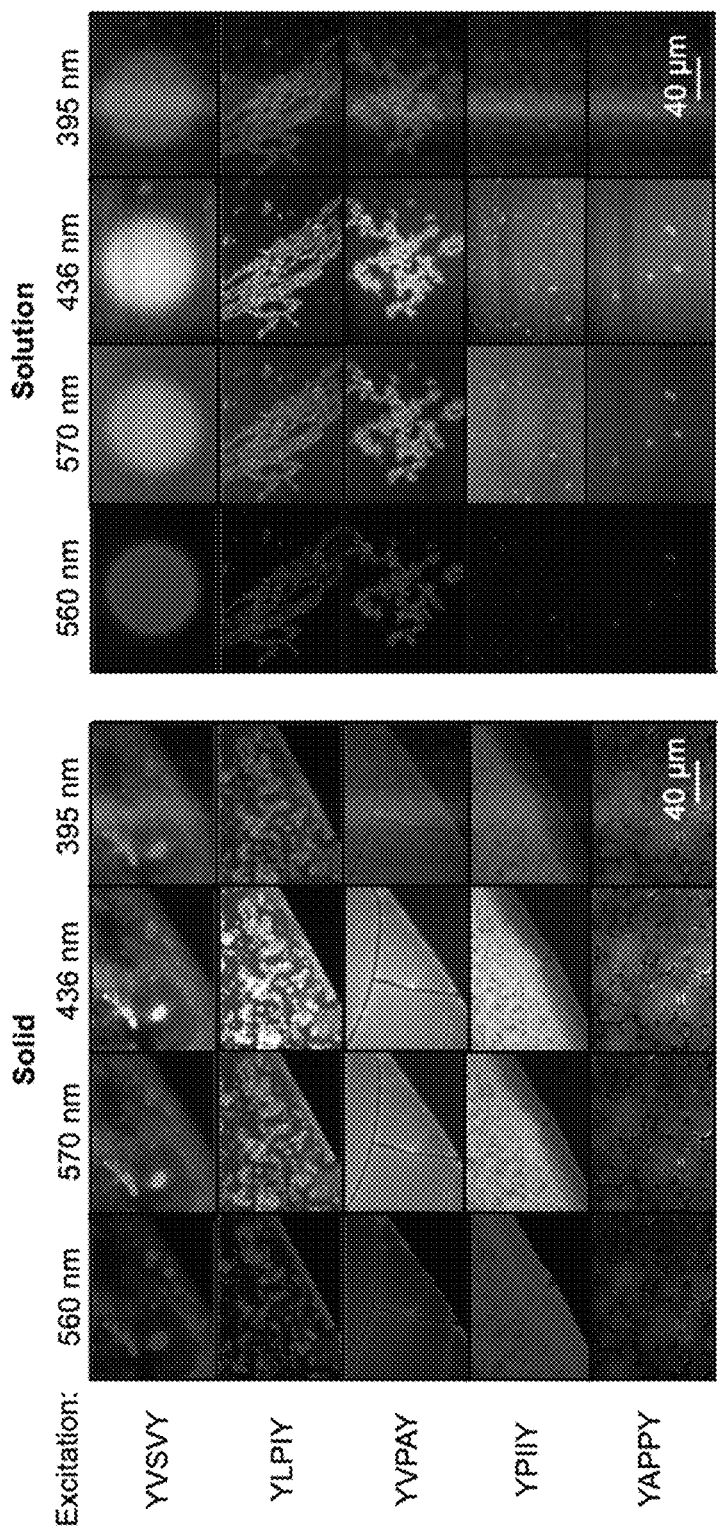

The subsequent challenge is whether their quantum-confined properties would be retained as these peptide nanoassemblies are scaled up into the microscale. Uncontrolled aggregation has been reported as the main culprit during this process as nanoparticles tend to uncontrollably and irreversibly merge into larger particles, causing them to lose their quantum-confined structures and properties (Ref 30). Each post-production enzymatically modified peptide was drop casted onto a glass slide and dried overnight at ambient temperature and pressure. Fluorescence microscopy was then used to characterize their microstructure and PL emission. See FIG. 7. Fluorescence characterization confirms that these enzymatic modified peptide assemblies were successfully scaled up into extended solid film, while preserving their quantum-confined PL properties (FIG. 3C). Their PL emissions were successfully retained across the entire visible spectrum.

Figure 8:
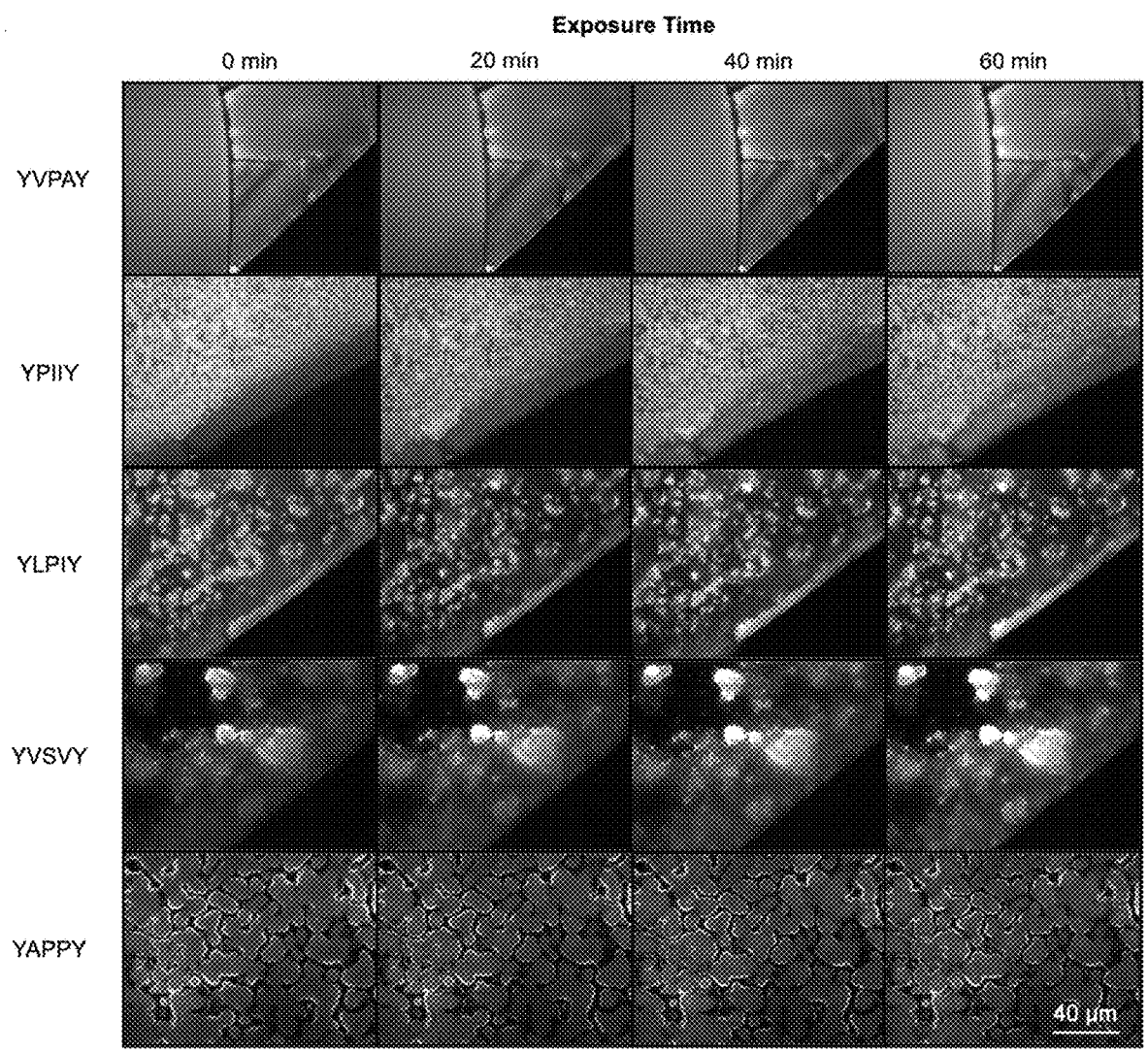
FIG. 8 depicts photobleaching of enzymatically modified peptide assemblies. Enzymatically modified peptide assemblies were exposed to UV irradiation under a fluorescence microscope for an hour. All subpanels reflect representative data from experiments repeated three times on different days (SEQ ID NOs. 5, 11, 8, 14, and 3, respectively, in order of appearance).
Figure 9:
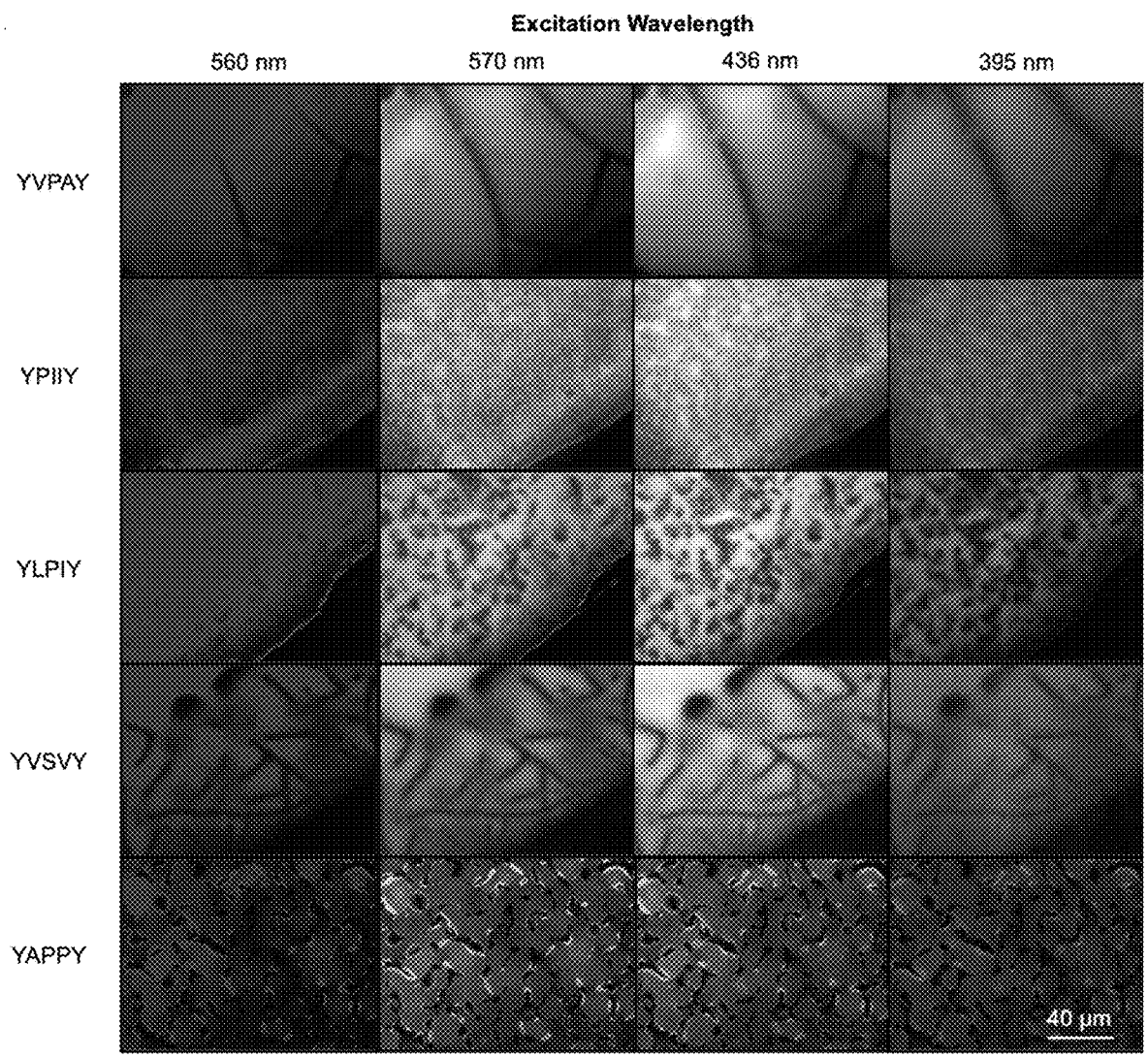
FIG. 9 depicts the thermal stability of enzymatically modified peptide assemblies. Enzymatically modified peptide assemblies were heated in an oven at 200° C. for 2 hours before fluorescence characterization using a fluorescence microscope. All subpanels reflect representative data from experiments repeated three times on different days (SEQ ID NOs. 5, 11, 8, 14, and 3, respectively, in order of appearance).

While inorganic materials show superior photothermal stability and minimal photobleaching even after prolonged UV exposure, many organic materials suffer from photobleaching and denature at high temperature. For example, inorganic CdSe/ZnS quantum dot can survive hours of UV exposure (Ref 31), but green fluorescent protein (GFP) can barely survive 1 second of UV irradiation (Ref. 32). The drop-casted solid film was exposed to UV irradiation for an hour under a fluorescence microscope. Incredibly, no photobleaching was observed in any of the enzymatic oxidized peptide assemblies even after prolonged UV exposure of an hour (FIG. 8). To test for thermal stability, the drop-casted peptide films were heated in an oven at 200° C. for 2 hours and then fluorescence characterization was performed (FIG. 9). While slight physical degradation was observed in YPIIY (SEQ ID NO. 11), YLPIY (SEQ ID NO. 8), YVSVY (SEQ ID NO. 14) especially at the film-glass interface, their PL property is intact.

Enzymatically Modified Peptide Assemblies as Amorphous Structural Pigments

Butterfly-inspired structural pigments that are environmentally friendly and fade-resistant have been long sought, but their angle-dependent optical properties and iridescence make them less useful (33-35). Suppressing iridescent effect while preserving the structural pigment optical properties is a big challenge, which we addressed by leveraging on the amorphous self-assembly of our enzymatically modified peptide assemblies to preserve their short-range order, while breaking down formation of the long-range order arrangement. High ions concentration (20 mM) was used during the peptide self-assembly process to increase electrostatic repulsion between them and to facilitate the breakdown of long-range order arrangement. After a few weeks of incubation at ambient conditions, peptide solutions with low SAPs, i.e. YVGVY (SEQ ID NO. 22), YGFHY (SEQ ID NO. 19) and YKVQY (SEQ ID NO. 20), that were originally red, orange or yellow were found to display vibrant structural colors that extend to green and grey-blue, while those with high SAPS retain their original colors. UV-vis spectroscopy was performed to measure their absorption spectra. One possible explanation on why only low SAP peptide sequences were able to extend structural coloration into the green region of the visible spectrum is that only peptides with low SAP were able to break down long-range order due to their loose amorphous structure, while high SAP sequences were more unlikely to break down long-range order due to their compact ordered structure.

Discussion

Figure 10:
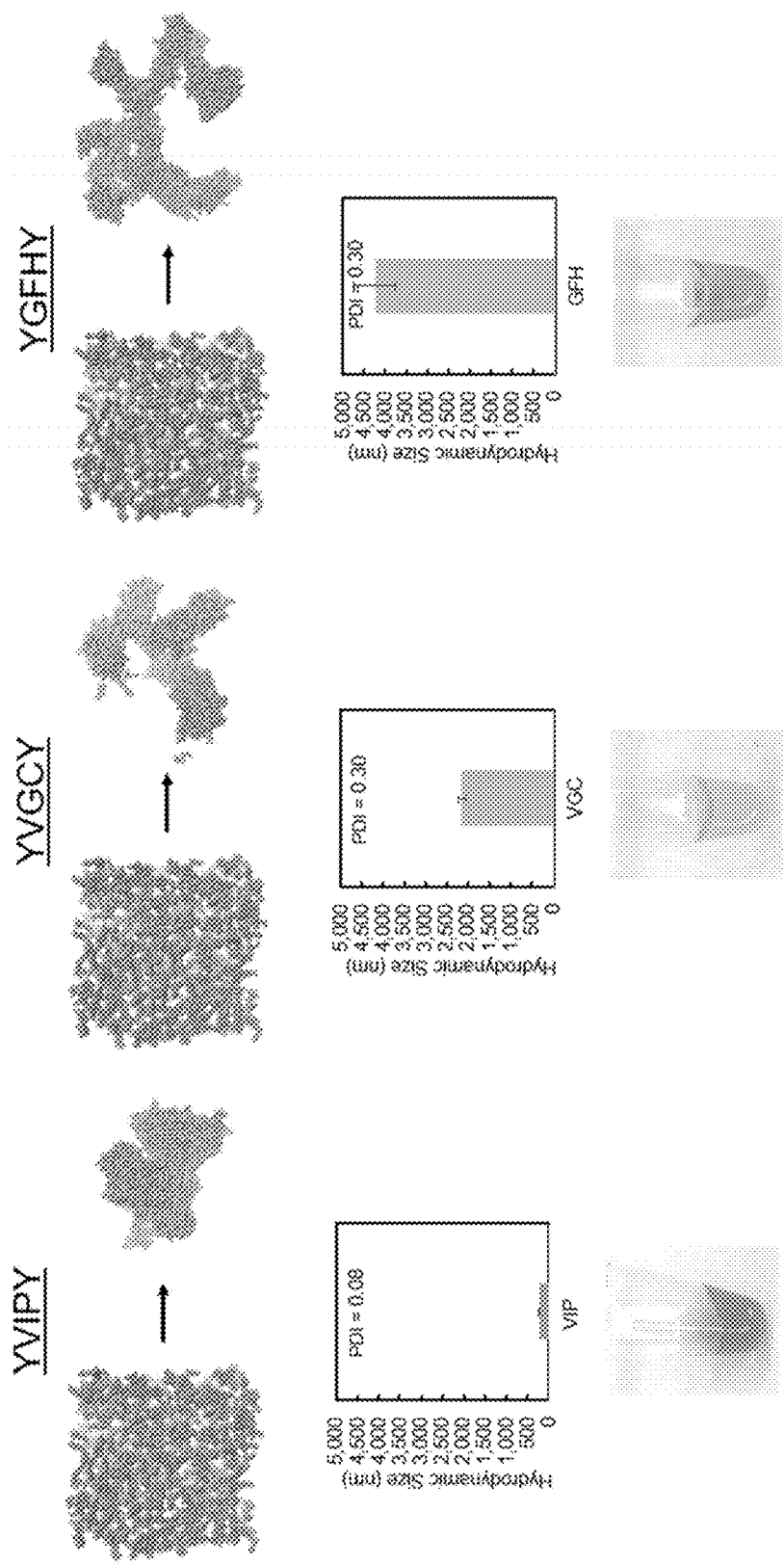
FIG. 10 depicts MD simulation, hydrodynamic radius and color of melanin peptides. The size of MD simulated structure is confirmed by hydrodynamic radius obtained from Dynamic Light Scattering (DLS) experiment. (SEQ ID NOs. 21, 18, and 19, respectively, in order of appearance).

The present disclosure describes the use of post-production enzymatic modification under ambient conditions to introduce aromatic, conjugated systems into quantum-confined peptide structures mined from computer simulations as an attempt to tune their optical and electronic properties that would otherwise require the use of expensive, environmentally damaging rare earth metals and inorganic materials. Martini force field simulations were performed to screen a library of 8,000 self-assembling short pentapeptides to mine peptide sequences with the potential to form quantum-confined structures. Using a short packing sequence of three amino acids is essential to prevent polymer-like properties that will compromise optical and electronic properties derived from quantum confinement effect. From the simulation results, it is evident that hydrophobic and short polar amino acids contribute to self-assembly, while charged and long polar residues compromise self-assembly. Quantum-confined peptides assemblies of various sizes and morphologies were successfully produced, and the peptide solutions turned from colorless to colored after enzymatic modification with tyrosinase enzyme. See, FIG. 10. Moreover, these peptides exhibit broad PL emission across the whole visible spectrum, while their individual emission intensity varies according to its sequence and structure. Post-production tyrosinase modification significantly enhanced their PL properties. Collectively, these results suggest that band gaps were formed in these enzymatic modified peptide assemblies, and that the introduction of conjugated systems together with quantum confinement effect were able to replicate quantum-confined properties observed in rare-earth-metal-based, inorganic nanoparticles (Ref 36).

Furthermore, these enzymatically modified peptide assemblies showed superior photothermal stability and minimal photobleaching, which are properties that can only be found in inorganic nanomaterials such as CdSe/ZnS quantum dot. Additionally, through the use of high ion concentration and low SAP peptide sequences to break down long-range order while preserving short-range order, vibrant structural colors ranging from red, orange, yellow, green to grey-blue were successfully produced.

In conclusion, our enzymatically modified peptide assemblies were found to possess some of the hallmark traits of rare-earth-based inorganic nanomaterials, while retaining the facile environmentally friendly production process of biological molecules that is highly scalable. These properties can even be tuned in a bottom-up manner from the peptide sequence level, opening the door to designing a plethora of rare-earth-free bionanomaterials that are highly scalable for applications in biomedical, electronic and photonic fields.

References, each of which is incorporated by reference in its entirety.

1. S. J. Lin, T. Y. Yu, Z. Y. Yu, X. L. Hu, D. Q. Yin, Nanomaterials Safer-by-Design: An Environmental Safety Perspective. *Advanced Materials* 30, (2018).
2. T. T. Y Tan, RARE EARTH NANOTECHNOLOGY Preface. *Rare Earth Nanotechnology*, Xi-Xii (2012).
3. V. L. Colvin, The potential environmental impact of engineered nanomaterials. *Nature Biotechnology* 21, 1166-1170 (2003).
4. V. Balaram, Rare earth elements: A review of applications, occurrence, exploration, analysis, recycling, and environmental impact. *Geosci Front* 10, 1285-1303 (2019).
5. A matter of scale. *Nature Nanotechnology* 11, 733-733 (2016).
6. W. J. Parak, A. E. Nel, P. S. Weiss, Grand Challenges for Nanoscience and Nanotechnology. *Acs Nano* 9, 6637-6640 (2015).
7. E. De Tommasi et al., UV-shielding and wavelength conversion by centric diatom nanopatterned frustules. *Scientific Reports* 8, (2018).
8. K. Chung et al., Flexible, Angle-Independent, Structural Color Reflectors Inspired by Morpho Butterfly Wings. *Advanced Materials* 24, 2375-2379 (2012).
9. R. L. Haining, C. Achat-Mendes, Neuromelanin, one of the most overlooked molecules in modern medicine, is not a spectator. *Neural Regen Res* 12, 372-375 (2017).
10. E. Gazit, Self-assembled peptide nanostructures: the design of molecular building blocks and their technological utilization. *Chemical Society Reviews* 36, 1263-1269 (2007).
11. G Wei et al., Self-assembling peptide and protein amyloids: from structure to tailored function in nanotechnology. *Chemical Society Reviews* 46, 4661-4708 (2017).
12. Y. Y. Wang, J. H. Pu, B. L. An, T. K. Lu, C. Zhong, Emerging Paradigms for Synthetic Design of Functional Amyloids. *Journal of Molecular Biology* 430, 3720-3734 (2018).
13. U. O. S. Seker, A. Y. Chen, R. J. Citorik, T. K. Lu, Synthetic Biogenesis of Bacterial Amyloid Nanomaterials with Tunable Inorganic-Organic Interfaces and Electrical Conductivity. *Acs Synthetic Biology* 6, 266-275 (2017).
14. T. Scheibel et al., Conducting nanowires built by controlled self-assembly of amyloid fibers and selective metal deposition. *Proceedings of the National Academy of Sciences of the United States of America* 100, 4527-4532 (2003).
15. N. L. Ing, M. Y El-Naggar, A. I. Hochbaum, Going the Distance: Long-Range Conductivity in Protein and Peptide Bioelectronic Materials. *Journal of Physical Chemistry B* 122, 10403-10423 (2018).
16. A. K. Wallace, N. Chanut, C. A. Voigt, Silica Nanostructures Produced Using Diatom Peptides with Designed Post-Translational Modifications. *Advanced Functional Materials* 30, (2020).
17. A. A. R. Watt, J. P. Bothma, P. Meredith, The supramolecular structure of melanin. *Soft Matter* 5, 3754-3760 (2009).
18. T. Strzelecka, A Band Model for Synthetic Dopa-Melanin. *Physiol Chem Phys M* 14, 219-222 (1982).
19. T. Strzelecka, Semiconductor Properties of Natural Melanins. *Physiol Chem Phys M* 14, 223-231 (1982).
20. A. B. Mostert et al., Role of semiconductivity and ion transport in the electrical conduction of melanin. *Proceedings of the National Academy of Sciences* 109, 8943 (2012).
21. W. Sajj ad et al., Pigment production by cold-adapted bacteria and fungi: colorful tale of cryosphere with wide range applications. *Extremophiles* 24, 447-473 (2020).
22. L. Selbmann, L. Zucconi, D. Isola, S. Onofri, Rock black fungi: excellence in the extremes, from the Antarctic to space. *Curr Genet* 61, 335-345 (2015).
23. E. Dadachova, A. Casadevall, Ionizing radiation: how fungi cope, adapt, and exploit with the help of melanin. *Curr Opin Microbiol* 11, 525-531 (2008).
24. N. N. Zhdanova, V. A. Zakharchenko, V. V. Vember, L. T. Nakonechnaya, Fungi from Chernobyl: mycobiota of the inner regions of the containment structures of the damaged nuclear reactor. *Mycol Res* 104, 1421-1426 (2000).
25. C. Pacelli et al., Cryptoendolithic Antarctic Black Fungus *Cryomyces antarcticus* Irradiated with Accelerated Helium Ions: Survival and Metabolic Activity, DNA and Ultrastructural Damage. *Front Microbiol* 8, (2017).
26. C. Pacelli et al., Responses of the Black Fungus Cryomyces antarcticus to Simulated Mars and Space Conditions on Rock Analogs. *Astrobiology* 19, 209-220 (2019).
27. R. J. B. Cordero, Melanin for space travel radioprotection. *Environ Microbiol* 19, 2529-2532 (2017).
28. P. W. Frederix et al., Exploring the sequence space for (tri-)peptide self-assembly to design and discover new hydrogels. *Nat Chem* 7, 30-37 (2015).
29. K. Tao et al., Quantum confined peptide assemblies with tunable visible to near-infrared spectral range. *Nat Commun* 9, 3217 (2018).
30. E. M. Hotze, T. Phenrat, G V. Lowry, Nanoparticle Aggregation: Challenges to Understanding Transport and Reactivity in the Environment. *Journal of Environmental Quality* 39, 1909-1924 (2010).
31. M. G Hyldahl, S. T. Bailey, B. P. Wittmershaus, Photostability and performance of CdSe/ZnS quantum dots in luminescent solar concentrators. *Solar Energy* 83, 566-573 (2009).
32. R. Y. Tsien, The green fluorescent protein. *Annual Review of Biochemistry* 67, 509-544 (1998).

33. L. Shi et al., Amorphous Photonic Crystals with Only Short-Range Order. *Advanced Materials* 25, 5314-5320 (2013).
34. Y. F. Zhang et al., Using Cuttlefish Ink as an Additive to Produce Non-iridescent Structural Colors of High Color Visibility. *Advanced Materials* 27, 4719-4724 (2015).
35. J. G Park et al., Full-Spectrum Photonic Pigments with Non-iridescent Structural Colors through Colloidal Assembly. *Angew Chem Int Edit* 53, 2899-2903 (2014).
36. U. Cho, J. K. Chen, Lanthanide-Based Optical Probes of Biological Systems. *Cell Chem Biol* 27, 921-936 (2020).

Figure 11:
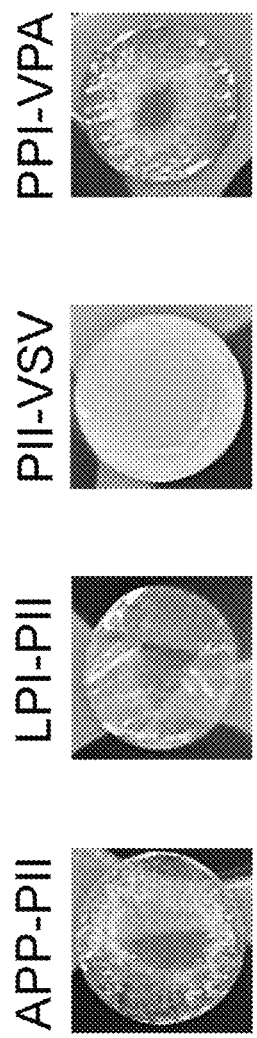
FIG. 11 depicts solid peptide films formed from 50/50 molar ratio of a pentapeptide mixture. The resulting mixture/films have a shiny, metallic appearance.

An example of a specular reflection structure is depicted in FIG. 11. Combinations of two pentapeptides, in a 50:50 molar ratio, followed by treatment with tyrosinase, results in a specular reflection structure. As shown in FIG. 11, solid peptide films formed from 50:50 molar ratio of pentapeptide mixtures have a shiny, metallic appearance.

Figure 12:
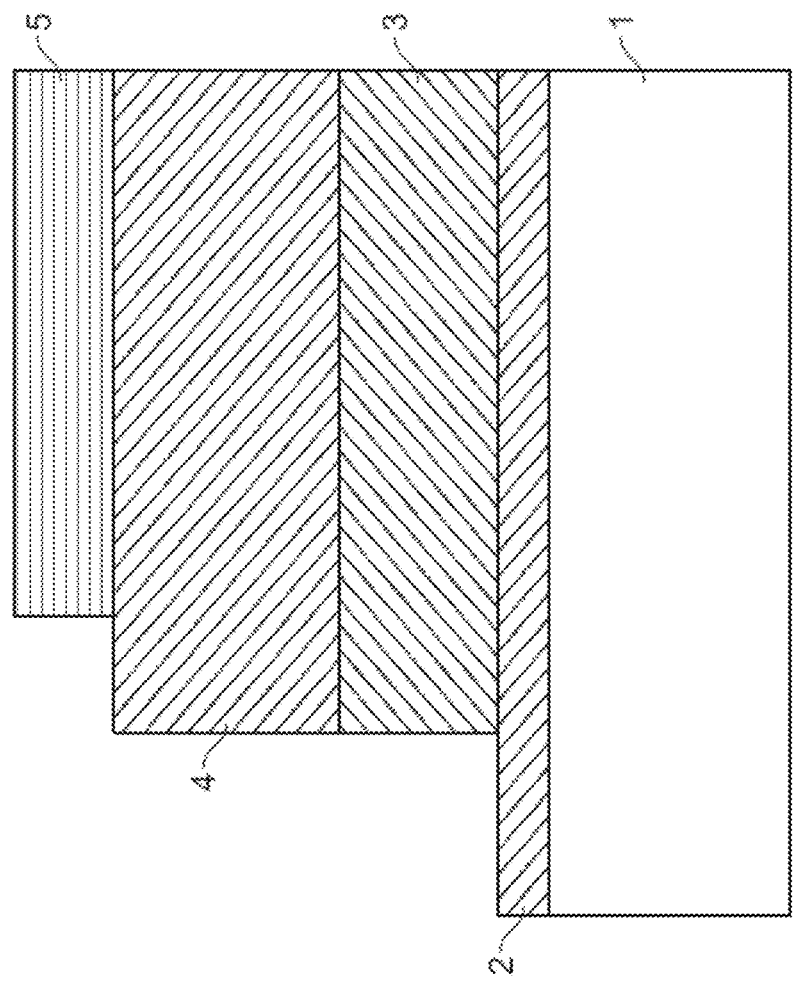
FIG. 12 is a schematic drawing depicting a display device.
Figure 13A:
FIGS. 13A-13D depict libraries of potential morphologies and potential structure-color relationships.
Figure 13B:
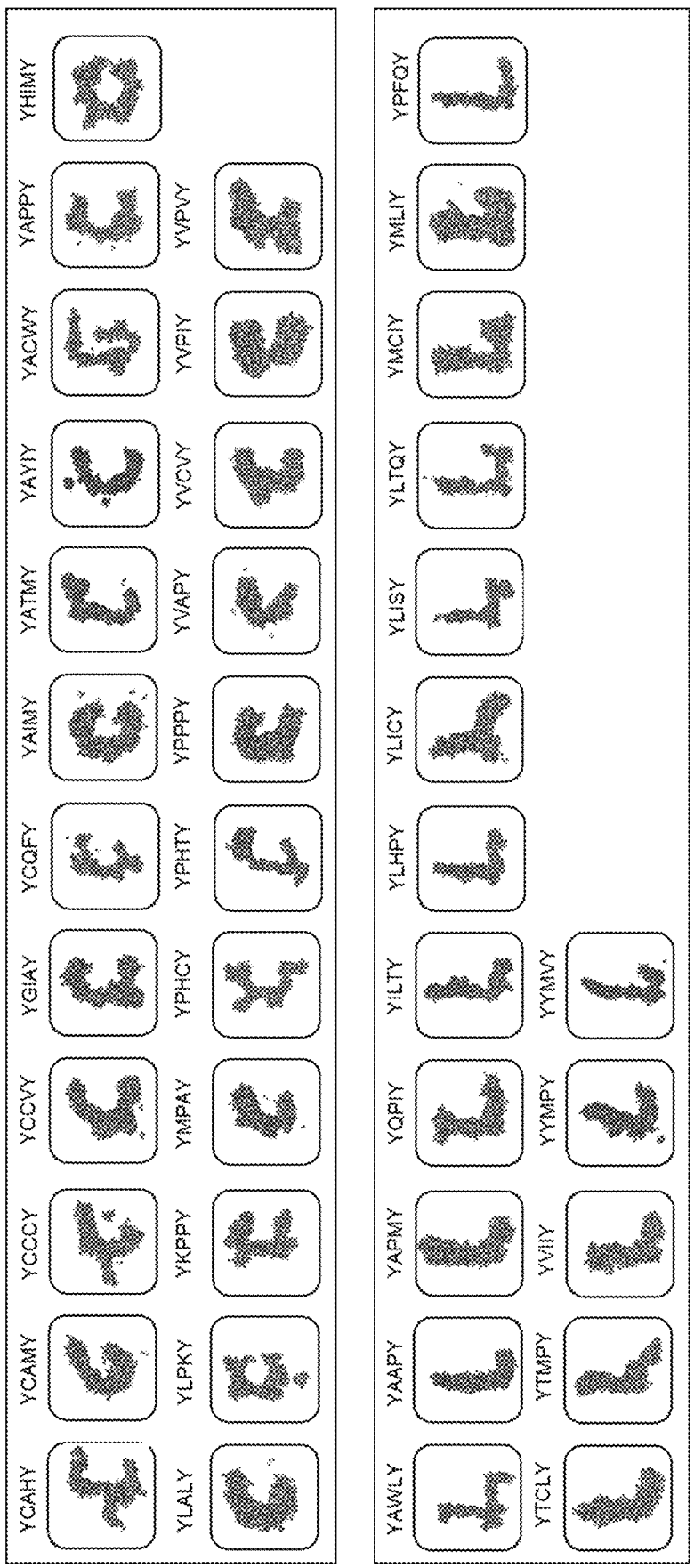
Figure 13C:
Figure 13D:

The structural colors described herein can be used in electrophoretic displays. For example, a display shown in FIG. 12 can include a structure in which a first electrode 2, a first layer 3 in contact with the electrode 2, an optional second layer 4 that can be in contact with the layer 3, and a second electrode 5 in contact with the second layer 4, if present, or layer 3. First layer 3 can include the structural color, for example, in an electrophoretic medium. If present, the second layer 4 can be a transparent sealing material to contain the electrophoretic medium. Electrode 5 is a transparent electrode. Each electrode can contact a power supply to provide a voltage across the structure. The structural color, for example, based on the polypeptide material described herein, can be made visible or not visible by applying voltage between the electrodes.

Details of one or more embodiments are set forth in the accompanying drawings and description. Other features, objects, and advantages will be apparent from the description, drawings, and claims. Although a number of embodiments of the invention have been described, it will be understood that various modifications may be made without departing from the spirit and scope of the invention. It should also be understood that the appended drawings are not necessarily to scale, presenting a somewhat simplified representation of various features and basic principles of the invention.

What is claimed is:

1. A composition comprising:
   a peptide self-assembly comprising a plurality of a peptide, the peptide having a packing sequence that includes no more than three amino acids,
   wherein the peptide further includes melanin derived from oxidation of tyrosine residues, the melanin providing an aromatic and conjugated system to the peptide self-assembly,
   wherein the packing sequence determines size, compacity, and morphology of the peptide self-assembly, and
   wherein the composition has a color provided by the aromatic and conjugated system of the peptide self-assembly.

2. The composition of claim 1, wherein the peptide is a pentapeptide.

3. The composition of claim 1, wherein the tyrosine residues are an N-terminal tyrosine and a C-terminal tyrosine.

4. The composition of claim 1, wherein the color of the composition is blue, green, yellow, orange, or red.

5. The composition of claim 4, wherein the blue is grey-blue.

6. The composition of claim 1, wherein the packing sequence contains valine, isoleucine, proline, or combinations thereof.

7. The composition of claim 1, wherein the peptide self-assembly has a 3D, 2D, 1D, or 0D morphology.

8. The composition of claim 7, wherein the 3D morphology is a globular structure, the 2D morphology is a sheet-like structure, the 1D morphology is a fiber-like structure, or the 0D morphology is a quantum dot-like structure.

9. The composition of claim 1, wherein the peptide has a low self-assembly potential (SAP).

10. The composition of claim 1, wherein the peptide has a high self-assembly potential (SAP).

11. The composition of claim 1, wherein the peptide self-assembly has a long-range order arrangement.

12. The composition of claim 1, wherein the peptide self-assembly has a short-range order arrangement.

13. The composition of claim 1, further comprising:
a plurality of a second peptide forming a second peptide self-assembly,
wherein the second peptide of the plurality includes melanin derived from oxidation of tyrosine residues.

14. The composition of claim 13, wherein the peptide and the second peptide are different peptides.

15. The composition of claim 13, wherein the peptide self-assembly and the second peptide self-assembly have the same morphology.

16. The composition of claim 13, wherein the peptide self-assembly and the second peptide self-assembly have the different morphology.

17. The composition of claim 1, wherein the peptide self-assembly is a peptide nanoassembly.

18. A colored device comprising:
a composition of claim 1.

19. The colored device of claim 18, wherein the device includes a first electrode, a second electrode and the composition between the first electrode and the second electrode.

\* \* \* \* \*

SEQUENCE LISTING

```
<160> NUMBER OF SEQ ID NOS: 160

<210> SEQ ID NO 1
<211> LENGTH: 5
<212> TYPE: PRT
<213> ORGANISM: Artificial Sequence
<220> FEATURE:
<223> OTHER INFORMATION: synthetic

<400> SEQUENCE: 1

Tyr Ile Ala Pro Tyr
1               5

<210> SEQ ID NO 2
<211> LENGTH: 5
<212> TYPE: PRT
<213> ORGANISM: Artificial Sequence
<220> FEATURE:
<223> OTHER INFORMATION: synthetic

<400> SEQUENCE: 2

Tyr Phe Pro Pro Tyr
1               5

<210> SEQ ID NO 3
<211> LENGTH: 5
<212> TYPE: PRT
<213> ORGANISM: Artificial Sequence
<220> FEATURE:
<223> OTHER INFORMATION: synthetic

<400> SEQUENCE: 3

Tyr Ala Pro Pro Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic

<400> SEQUENCE: 4
```

-continued

Tyr Ile Leu Pro Tyr
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic

<400> SEQUENCE: 5

Tyr Val Pro Ala Tyr
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic

<400> SEQUENCE: 6

Tyr Ala Pro Val Tyr
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic

<400> SEQUENCE: 7

Tyr Val Ile Pro Tyr
1               5

<210> SEQ ID NO 8
<211> LENGTH: 5
<212> TYPE: PRT
<213> ORGANISM: Artificial Sequence
<220> FEATURE:
<223> OTHER INFORMATION: synthetic

<400> SEQUENCE: 8

Tyr Leu Pro Ile Tyr
1               5

<210> SEQ ID NO 9
<211> LENGTH: 5
<212> TYPE: PRT
<213> ORGANISM: Artificial Sequence
<220> FEATURE:
<223> OTHER INFORMATION: synthetic

<400> SEQUENCE: 9

Tyr Pro Met Leu Tyr
1               5

<210> SEQ ID NO 10
<211> LENGTH: 5
<212> TYPE: PRT
<213> ORGANISM: Artificial Sequence
<220> FEATURE:
<223> OTHER INFORMATION: synthetic

<400> SEQUENCE: 10

Tyr Pro Pro Leu Tyr

```
1               5

<210> SEQ ID NO 11
<211> LENGTH: 5
<212> TYPE: PRT
<213> ORGANISM: Artificial Sequence
<220> FEATURE:
<223> OTHER INFORMATION: synthetic

<400> SEQUENCE: 11

Tyr Pro Ile Ile Tyr
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic

<400> SEQUENCE: 12

Tyr Pro Val Leu Tyr
1               5

<210> SEQ ID NO 13
<211> LENGTH: 5
<212> TYPE: PRT
<213> ORGANISM: Artificial Sequence
<220> FEATURE:
<223> OTHER INFORMATION: synthetic

<400> SEQUENCE: 13

Tyr Pro Pro Val Tyr
1               5

<210> SEQ ID NO 14
<211> LENGTH: 5
<212> TYPE: PRT
<213> ORGANISM: Artificial Sequence
<220> FEATURE:
<223> OTHER INFORMATION: synthetic

<400> SEQUENCE: 14

Tyr Val Ser Val Tyr
1               5

<210> SEQ ID NO 15
<211> LENGTH: 5
<212> TYPE: PRT
<213> ORGANISM: Artificial Sequence
<220> FEATURE:
<223> OTHER INFORMATION: synthetic

<400> SEQUENCE: 15

Tyr Gly Phe Glu Tyr
1               5

<210> SEQ ID NO 16
<211> LENGTH: 5
<212> TYPE: PRT
<213> ORGANISM: Artificial Sequence
<220> FEATURE:
<223> OTHER INFORMATION: synthetic

<400> SEQUENCE: 16

Tyr Ile Cys Pro Tyr
1               5
```

```
<210> SEQ ID NO 17
<211> LENGTH: 5
<212> TYPE: PRT
<213> ORGANISM: Artificial Sequence
<220> FEATURE:
<223> OTHER INFORMATION: synthetic

<400> SEQUENCE: 17

Tyr Cys Leu Ile Tyr
1               5

<210> SEQ ID NO 18
<211> LENGTH: 5
<212> TYPE: PRT
<213> ORGANISM: Artificial Sequence
<220> FEATURE:
<223> OTHER INFORMATION: synthetic

<400> SEQUENCE: 18

Tyr Val Gly Cys Tyr
1               5

<210> SEQ ID NO 19
<211> LENGTH: 5
<212> TYPE: PRT
<213> ORGANISM: Artificial Sequence
<220> FEATURE:
<223> OTHER INFORMATION: synthetic

<400> SEQUENCE: 19

Tyr Gly Phe His Tyr
1               5

<210> SEQ ID NO 20
<211> LENGTH: 5
<212> TYPE: PRT
<213> ORGANISM: Artificial Sequence
<220> FEATURE:
<223> OTHER INFORMATION: synthetic

<400> SEQUENCE: 20

Tyr Lys Val Gln Tyr
1               5

<210> SEQ ID NO 21
<211> LENGTH: 5
<212> TYPE: PRT
<213> ORGANISM: Artificial Sequence
<220> FEATURE:
<223> OTHER INFORMATION: synthetic

<400> SEQUENCE: 21

Tyr Val Ile Pro Tyr
1               5

<210> SEQ ID NO 22
<211> LENGTH: 5
<212> TYPE: PRT
<213> ORGANISM: Artificial Sequence
<220> FEATURE:
<223> OTHER INFORMATION: synthetic

<400> SEQUENCE: 22

Tyr Val Gly Val Tyr
1               5
```

```
<210> SEQ ID NO 23
<211> LENGTH: 5
<212> TYPE: PRT
<213> ORGANISM: Artificial Sequence
<220> FEATURE:
<223> OTHER INFORMATION: synthetic

<400> SEQUENCE: 23

Tyr Pro Pro Pro Tyr
1               5

<210> SEQ ID NO 24
<211> LENGTH: 5
<212> TYPE: PRT
<213> ORGANISM: Artificial Sequence
<220> FEATURE:
<223> OTHER INFORMATION: synthetic

<400> SEQUENCE: 24

Tyr Pro Met Leu Tyr
1               5

<210> SEQ ID NO 25
<211> LENGTH: 5
<212> TYPE: PRT
<213> ORGANISM: Artificial Sequence
<220> FEATURE:
<223> OTHER INFORMATION: synthetic

<400> SEQUENCE: 25

Tyr Cys Ala His Tyr
1               5

<210> SEQ ID NO 26
<211> LENGTH: 5
<212> TYPE: PRT
<213> ORGANISM: Artificial Sequence
<220> FEATURE:
<223> OTHER INFORMATION: synthetic

<400> SEQUENCE: 26

Tyr Cys Ala Met Tyr
1               5

<210> SEQ ID NO 27
<211> LENGTH: 5
<212> TYPE: PRT
<213> ORGANISM: Artificial Sequence
<220> FEATURE:
<223> OTHER INFORMATION: synthetic

<400> SEQUENCE: 27

Tyr Cys Cys Cys Tyr
1               5

<210> SEQ ID NO 28
<211> LENGTH: 5
<212> TYPE: PRT
<213> ORGANISM: Artificial Sequence
<220> FEATURE:
<223> OTHER INFORMATION: synthetic

<400> SEQUENCE: 28

Tyr Cys Cys Val Tyr
1               5
```

-continued

```
<210> SEQ ID NO 29
<211> LENGTH: 5
<212> TYPE: PRT
<213> ORGANISM: Artificial Sequence
<220> FEATURE:
<223> OTHER INFORMATION: synthetic

<400> SEQUENCE: 29

Tyr Gly Ile Ala Tyr
1               5

<210> SEQ ID NO 30
<211> LENGTH: 5
<212> TYPE: PRT
<213> ORGANISM: Artificial Sequence
<220> FEATURE:
<223> OTHER INFORMATION: synthetic

<400> SEQUENCE: 30

Tyr Cys Gln Phe Tyr
1               5

<210> SEQ ID NO 31
<211> LENGTH: 5
<212> TYPE: PRT
<213> ORGANISM: Artificial Sequence
<220> FEATURE:
<223> OTHER INFORMATION: synthetic

<400> SEQUENCE: 31

Tyr Ala Ile Met Tyr
1               5

<210> SEQ ID NO 32
<211> LENGTH: 5
<212> TYPE: PRT
<213> ORGANISM: Artificial Sequence
<220> FEATURE:
<223> OTHER INFORMATION: synthetic

<400> SEQUENCE: 32

Tyr Ala Thr Met Tyr
1               5

<210> SEQ ID NO 33
<211> LENGTH: 5
<212> TYPE: PRT
<213> ORGANISM: Artificial Sequence
<220> FEATURE:
<223> OTHER INFORMATION: synthetic

<400> SEQUENCE: 33

Tyr Ala Tyr Ile Tyr
1               5

<210> SEQ ID NO 34
<211> LENGTH: 5
<212> TYPE: PRT
<213> ORGANISM: Artificial Sequence
<220> FEATURE:
<223> OTHER INFORMATION: synthetic

<400> SEQUENCE: 34

Tyr Ala Cys Trp Tyr
1               5

<210> SEQ ID NO 35
```

```
<211> LENGTH: 5
<212> TYPE: PRT
<213> ORGANISM: Artificial Sequence
<220> FEATURE:
<223> OTHER INFORMATION: synthetic

<400> SEQUENCE: 35

Tyr His Ile Met Tyr
1               5

<210> SEQ ID NO 36
<211> LENGTH: 5
<212> TYPE: PRT
<213> ORGANISM: Artificial Sequence
<220> FEATURE:
<223> OTHER INFORMATION: synthetic

<400> SEQUENCE: 36

Tyr Leu Ala Leu Tyr
1               5

<210> SEQ ID NO 37
<211> LENGTH: 5
<212> TYPE: PRT
<213> ORGANISM: Artificial Sequence
<220> FEATURE:
<223> OTHER INFORMATION: synthetic

<400> SEQUENCE: 37

Tyr Leu Pro Lys Tyr
1               5

<210> SEQ ID NO 38
<211> LENGTH: 5
<212> TYPE: PRT
<213> ORGANISM: Artificial Sequence
<220> FEATURE:
<223> OTHER INFORMATION: synthetic

<400> SEQUENCE: 38

Tyr Lys Pro Pro Tyr
1               5

<210> SEQ ID NO 39
<211> LENGTH: 5
<212> TYPE: PRT
<213> ORGANISM: Artificial Sequence
<220> FEATURE:
<223> OTHER INFORMATION: synthetic

<400> SEQUENCE: 39

Tyr Met Pro Ala Tyr
1               5

<210> SEQ ID NO 40
<211> LENGTH: 5
<212> TYPE: PRT
<213> ORGANISM: Artificial Sequence
<220> FEATURE:
<223> OTHER INFORMATION: synthetic

<400> SEQUENCE: 40

Tyr Pro His Cys Tyr
1               5

<210> SEQ ID NO 41
<211> LENGTH: 5
```

```
<212> TYPE: PRT
<213> ORGANISM: Artificial Sequence
<220> FEATURE:
<223> OTHER INFORMATION: synthetic

<400> SEQUENCE: 41

Tyr Pro His Thr Tyr
1               5

<210> SEQ ID NO 42
<211> LENGTH: 5
<212> TYPE: PRT
<213> ORGANISM: Artificial Sequence
<220> FEATURE:
<223> OTHER INFORMATION: synthetic

<400> SEQUENCE: 42

Tyr Val Ala Pro Tyr
1               5

<210> SEQ ID NO 43
<211> LENGTH: 5
<212> TYPE: PRT
<213> ORGANISM: Artificial Sequence
<220> FEATURE:
<223> OTHER INFORMATION: synthetic

<400> SEQUENCE: 43

Tyr Val Cys Val Tyr
1               5

<210> SEQ ID NO 44
<211> LENGTH: 5
<212> TYPE: PRT
<213> ORGANISM: Artificial Sequence
<220> FEATURE:
<223> OTHER INFORMATION: synthetic

<400> SEQUENCE: 44

Tyr Val Pro Ile Tyr
1               5

<210> SEQ ID NO 45
<211> LENGTH: 5
<212> TYPE: PRT
<213> ORGANISM: Artificial Sequence
<220> FEATURE:
<223> OTHER INFORMATION: synthetic

<400> SEQUENCE: 45

Tyr Val Pro Val Tyr
1               5

<210> SEQ ID NO 46
<211> LENGTH: 5
<212> TYPE: PRT
<213> ORGANISM: Artificial Sequence
<220> FEATURE:
<223> OTHER INFORMATION: synthetic

<400> SEQUENCE: 46

Tyr Ala Trp Leu Tyr
1               5

<210> SEQ ID NO 47
<211> LENGTH: 5
<212> TYPE: PRT
```

```
<213> ORGANISM: Artificial Sequence
<220> FEATURE:
<223> OTHER INFORMATION: synthetic

<400> SEQUENCE: 47

Tyr Ala Ala Pro Tyr
1               5

<210> SEQ ID NO 48
<211> LENGTH: 5
<212> TYPE: PRT
<213> ORGANISM: Artificial Sequence
<220> FEATURE:
<223> OTHER INFORMATION: synthetic

<400> SEQUENCE: 48

Tyr Ala Pro Met Tyr
1               5

<210> SEQ ID NO 49
<211> LENGTH: 5
<212> TYPE: PRT
<213> ORGANISM: Artificial Sequence
<220> FEATURE:
<223> OTHER INFORMATION: synthetic

<400> SEQUENCE: 49

Tyr Gln Pro Ile Tyr
1               5

<210> SEQ ID NO 50
<211> LENGTH: 5
<212> TYPE: PRT
<213> ORGANISM: Artificial Sequence
<220> FEATURE:
<223> OTHER INFORMATION: synthetic

<400> SEQUENCE: 50

Tyr Ile Leu Thr Tyr
1               5

<210> SEQ ID NO 51
<211> LENGTH: 5
<212> TYPE: PRT
<213> ORGANISM: Artificial Sequence
<220> FEATURE:
<223> OTHER INFORMATION: synthetic

<400> SEQUENCE: 51

Tyr Leu His Pro Tyr
1               5

<210> SEQ ID NO 52
<211> LENGTH: 5
<212> TYPE: PRT
<213> ORGANISM: Artificial Sequence
<220> FEATURE:
<223> OTHER INFORMATION: synthetic

<400> SEQUENCE: 52

Tyr Leu Ile Cys Tyr
1               5

<210> SEQ ID NO 53
<211> LENGTH: 5
<212> TYPE: PRT
<213> ORGANISM: Artificial Sequence
```

<220> FEATURE:
<223> OTHER INFORMATION: synthetic

<400> SEQUENCE: 53

Tyr Leu Ile Ser Tyr
1               5

<210> SEQ ID NO 54
<211> LENGTH: 5
<212> TYPE: PRT
<213> ORGANISM: Artificial Sequence
<220> FEATURE:
<223> OTHER INFORMATION: synthetic

<400> SEQUENCE: 54

Tyr Leu Thr Gln Tyr
1               5

<210> SEQ ID NO 55
<211> LENGTH: 5
<212> TYPE: PRT
<213> ORGANISM: Artificial Sequence
<220> FEATURE:
<223> OTHER INFORMATION: synthetic

<400> SEQUENCE: 55

Tyr Met Cys Ile Tyr
1               5

<210> SEQ ID NO 56
<211> LENGTH: 5
<212> TYPE: PRT
<213> ORGANISM: Artificial Sequence
<220> FEATURE:
<223> OTHER INFORMATION: synthetic

<400> SEQUENCE: 56

Tyr Met Leu Ile Tyr
1               5

<210> SEQ ID NO 57
<211> LENGTH: 5
<212> TYPE: PRT
<213> ORGANISM: Artificial Sequence
<220> FEATURE:
<223> OTHER INFORMATION: synthetic

<400> SEQUENCE: 57

Tyr Pro Phe Gln Tyr
1               5

<210> SEQ ID NO 58
<211> LENGTH: 5
<212> TYPE: PRT
<213> ORGANISM: Artificial Sequence
<220> FEATURE:
<223> OTHER INFORMATION: synthetic

<400> SEQUENCE: 58

Tyr Thr Cys Leu Tyr
1               5

<210> SEQ ID NO 59
<211> LENGTH: 5
<212> TYPE: PRT
<213> ORGANISM: Artificial Sequence
<220> FEATURE:

<223> OTHER INFORMATION: synthetic

<400> SEQUENCE: 59

Tyr Thr Met Pro Tyr
1               5

<210> SEQ ID NO 60
<211> LENGTH: 5
<212> TYPE: PRT
<213> ORGANISM: Artificial Sequence
<220> FEATURE:
<223> OTHER INFORMATION: synthetic

<400> SEQUENCE: 60

Tyr Val Ile Ile Tyr
1               5

<210> SEQ ID NO 61
<211> LENGTH: 5
<212> TYPE: PRT
<213> ORGANISM: Artificial Sequence
<220> FEATURE:
<223> OTHER INFORMATION: synthetic

<400> SEQUENCE: 61

Tyr Tyr Met Pro Tyr
1               5

<210> SEQ ID NO 62
<211> LENGTH: 5
<212> TYPE: PRT
<213> ORGANISM: Artificial Sequence
<220> FEATURE:
<223> OTHER INFORMATION: synthetic

<400> SEQUENCE: 62

Tyr Tyr Met Val Tyr
1               5

<210> SEQ ID NO 63
<211> LENGTH: 5
<212> TYPE: PRT
<213> ORGANISM: Artificial Sequence
<220> FEATURE:
<223> OTHER INFORMATION: synthetic

<400> SEQUENCE: 63

Tyr Ala Val Met Tyr
1               5

<210> SEQ ID NO 64
<211> LENGTH: 5
<212> TYPE: PRT
<213> ORGANISM: Artificial Sequence
<220> FEATURE:
<223> OTHER INFORMATION: synthetic

<400> SEQUENCE: 64

Tyr Cys Ala Cys Tyr
1               5

<210> SEQ ID NO 65
<211> LENGTH: 5
<212> TYPE: PRT
<213> ORGANISM: Artificial Sequence
<220> FEATURE:
<223> OTHER INFORMATION: synthetic

```
<400> SEQUENCE: 65

Tyr Gly Ile Phe Tyr
1               5

<210> SEQ ID NO 66
<211> LENGTH: 5
<212> TYPE: PRT
<213> ORGANISM: Artificial Sequence
<220> FEATURE:
<223> OTHER INFORMATION: synthetic

<400> SEQUENCE: 66

Tyr Ala Phe Ile Tyr
1               5

<210> SEQ ID NO 67
<211> LENGTH: 5
<212> TYPE: PRT
<213> ORGANISM: Artificial Sequence
<220> FEATURE:
<223> OTHER INFORMATION: synthetic

<400> SEQUENCE: 67

Tyr Cys Pro Trp Tyr
1               5

<210> SEQ ID NO 68
<211> LENGTH: 5
<212> TYPE: PRT
<213> ORGANISM: Artificial Sequence
<220> FEATURE:
<223> OTHER INFORMATION: synthetic

<400> SEQUENCE: 68

Tyr Ile Tyr Leu Tyr
1               5

<210> SEQ ID NO 69
<211> LENGTH: 5
<212> TYPE: PRT
<213> ORGANISM: Artificial Sequence
<220> FEATURE:
<223> OTHER INFORMATION: synthetic

<400> SEQUENCE: 69

Tyr Ile Val Cys Tyr
1               5

<210> SEQ ID NO 70
<211> LENGTH: 5
<212> TYPE: PRT
<213> ORGANISM: Artificial Sequence
<220> FEATURE:
<223> OTHER INFORMATION: synthetic

<400> SEQUENCE: 70

Tyr Met Pro Ser Tyr
1               5

<210> SEQ ID NO 71
<211> LENGTH: 5
<212> TYPE: PRT
<213> ORGANISM: Artificial Sequence
<220> FEATURE:
<223> OTHER INFORMATION: synthetic
```

```
<400> SEQUENCE: 71

Tyr Pro Gln Trp Tyr
1               5

<210> SEQ ID NO 72
<211> LENGTH: 5
<212> TYPE: PRT
<213> ORGANISM: Artificial Sequence
<220> FEATURE:
<223> OTHER INFORMATION: synthetic

<400> SEQUENCE: 72

Tyr Pro Thr Cys Tyr
1               5

<210> SEQ ID NO 73
<211> LENGTH: 5
<212> TYPE: PRT
<213> ORGANISM: Artificial Sequence
<220> FEATURE:
<223> OTHER INFORMATION: synthetic

<400> SEQUENCE: 73

Tyr Thr Leu Ile Tyr
1               5

<210> SEQ ID NO 74
<211> LENGTH: 5
<212> TYPE: PRT
<213> ORGANISM: Artificial Sequence
<220> FEATURE:
<223> OTHER INFORMATION: synthetic

<400> SEQUENCE: 74

Tyr Val Leu Pro Tyr
1               5

<210> SEQ ID NO 75
<211> LENGTH: 5
<212> TYPE: PRT
<213> ORGANISM: Artificial Sequence
<220> FEATURE:
<223> OTHER INFORMATION: synthetic

<400> SEQUENCE: 75

Tyr Val Met Pro Tyr
1               5

<210> SEQ ID NO 76
<211> LENGTH: 5
<212> TYPE: PRT
<213> ORGANISM: Artificial Sequence
<220> FEATURE:
<223> OTHER INFORMATION: synthetic

<400> SEQUENCE: 76

Tyr Trp Ile Val Tyr
1               5

<210> SEQ ID NO 77
<211> LENGTH: 5
<212> TYPE: PRT
<213> ORGANISM: Artificial Sequence
<220> FEATURE:
<223> OTHER INFORMATION: synthetic

<400> SEQUENCE: 77
```

```
Tyr Tyr Leu Ala Tyr
1               5

<210> SEQ ID NO 78
<211> LENGTH: 5
<212> TYPE: PRT
<213> ORGANISM: Artificial Sequence
<220> FEATURE:
<223> OTHER INFORMATION: synthetic

<400> SEQUENCE: 78

Tyr Ala Ser Trp Tyr
1               5

<210> SEQ ID NO 79
<211> LENGTH: 5
<212> TYPE: PRT
<213> ORGANISM: Artificial Sequence
<220> FEATURE:
<223> OTHER INFORMATION: synthetic

<400> SEQUENCE: 79

Tyr Gln Pro Pro Tyr
1               5

<210> SEQ ID NO 80
<211> LENGTH: 5
<212> TYPE: PRT
<213> ORGANISM: Artificial Sequence
<220> FEATURE:
<223> OTHER INFORMATION: synthetic

<400> SEQUENCE: 80

Tyr Cys Ile Ser Tyr
1               5

<210> SEQ ID NO 81
<211> LENGTH: 5
<212> TYPE: PRT
<213> ORGANISM: Artificial Sequence
<220> FEATURE:
<223> OTHER INFORMATION: synthetic

<400> SEQUENCE: 81

Tyr Gly Phe Tyr Tyr
1               5

<210> SEQ ID NO 82
<211> LENGTH: 5
<212> TYPE: PRT
<213> ORGANISM: Artificial Sequence
<220> FEATURE:
<223> OTHER INFORMATION: synthetic

<400> SEQUENCE: 82

Tyr Gly Ser Asn Tyr
1               5

<210> SEQ ID NO 83
<211> LENGTH: 5
<212> TYPE: PRT
<213> ORGANISM: Artificial Sequence
<220> FEATURE:
<223> OTHER INFORMATION: synthetic

<400> SEQUENCE: 83
```

```
Tyr Ile Leu Met Tyr
1               5

<210> SEQ ID NO 84
<211> LENGTH: 5
<212> TYPE: PRT
<213> ORGANISM: Artificial Sequence
<220> FEATURE:
<223> OTHER INFORMATION: synthetic

<400> SEQUENCE: 84

Tyr Ile Phe Leu Tyr
1               5

<210> SEQ ID NO 85
<211> LENGTH: 5
<212> TYPE: PRT
<213> ORGANISM: Artificial Sequence
<220> FEATURE:
<223> OTHER INFORMATION: synthetic

<400> SEQUENCE: 85

Tyr Leu Ala Met Tyr
1               5

<210> SEQ ID NO 86
<211> LENGTH: 5
<212> TYPE: PRT
<213> ORGANISM: Artificial Sequence
<220> FEATURE:
<223> OTHER INFORMATION: synthetic

<400> SEQUENCE: 86

Tyr Leu Gly Phe Tyr
1               5

<210> SEQ ID NO 87
<211> LENGTH: 5
<212> TYPE: PRT
<213> ORGANISM: Artificial Sequence
<220> FEATURE:
<223> OTHER INFORMATION: synthetic

<400> SEQUENCE: 87

Tyr Leu Ile Ala Tyr
1               5

<210> SEQ ID NO 88
<211> LENGTH: 5
<212> TYPE: PRT
<213> ORGANISM: Artificial Sequence
<220> FEATURE:
<223> OTHER INFORMATION: synthetic

<400> SEQUENCE: 88

Tyr Lys Leu Pro Tyr
1               5

<210> SEQ ID NO 89
<211> LENGTH: 5
<212> TYPE: PRT
<213> ORGANISM: Artificial Sequence
<220> FEATURE:
<223> OTHER INFORMATION: synthetic

<400> SEQUENCE: 89

Tyr Phe Val Pro Tyr
```

```
1               5

<210> SEQ ID NO 90
<211> LENGTH: 5
<212> TYPE: PRT
<213> ORGANISM: Artificial Sequence
<220> FEATURE:
<223> OTHER INFORMATION: synthetic

<400> SEQUENCE: 90

Tyr Pro His Asn Tyr
1               5

<210> SEQ ID NO 91
<211> LENGTH: 5
<212> TYPE: PRT
<213> ORGANISM: Artificial Sequence
<220> FEATURE:
<223> OTHER INFORMATION: synthetic

<400> SEQUENCE: 91

Tyr Pro Ile His Tyr
1               5

<210> SEQ ID NO 92
<211> LENGTH: 5
<212> TYPE: PRT
<213> ORGANISM: Artificial Sequence
<220> FEATURE:
<223> OTHER INFORMATION: synthetic

<400> SEQUENCE: 92

Tyr Thr Met Cys Tyr
1               5

<210> SEQ ID NO 93
<211> LENGTH: 5
<212> TYPE: PRT
<213> ORGANISM: Artificial Sequence
<220> FEATURE:
<223> OTHER INFORMATION: synthetic

<400> SEQUENCE: 93

Tyr Thr Val Ile Tyr
1               5

<210> SEQ ID NO 94
<211> LENGTH: 5
<212> TYPE: PRT
<213> ORGANISM: Artificial Sequence
<220> FEATURE:
<223> OTHER INFORMATION: synthetic

<400> SEQUENCE: 94

Tyr Thr Val Leu Tyr
1               5

<210> SEQ ID NO 95
<211> LENGTH: 5
<212> TYPE: PRT
<213> ORGANISM: Artificial Sequence
<220> FEATURE:
<223> OTHER INFORMATION: synthetic

<400> SEQUENCE: 95

Tyr Val Ile Leu Tyr
1               5
```

<210> SEQ ID NO 96
<211> LENGTH: 5
<212> TYPE: PRT
<213> ORGANISM: Artificial Sequence
<220> FEATURE:
<223> OTHER INFORMATION: synthetic

<400> SEQUENCE: 96

Tyr Val Pro Ser Tyr
1               5

<210> SEQ ID NO 97
<211> LENGTH: 5
<212> TYPE: PRT
<213> ORGANISM: Artificial Sequence
<220> FEATURE:
<223> OTHER INFORMATION: synthetic

<400> SEQUENCE: 97

Tyr Trp Gly Pro Tyr
1               5

<210> SEQ ID NO 98
<211> LENGTH: 5
<212> TYPE: PRT
<213> ORGANISM: Artificial Sequence
<220> FEATURE:
<223> OTHER INFORMATION: synthetic

<400> SEQUENCE: 98

Tyr Thr Pro Leu Tyr
1               5

<210> SEQ ID NO 99
<211> LENGTH: 5
<212> TYPE: PRT
<213> ORGANISM: Artificial Sequence
<220> FEATURE:
<223> OTHER INFORMATION: synthetic

<400> SEQUENCE: 99

Tyr Ile Pro Cys Tyr
1               5

<210> SEQ ID NO 100
<211> LENGTH: 5
<212> TYPE: PRT
<213> ORGANISM: Artificial Sequence
<220> FEATURE:
<223> OTHER INFORMATION: synthetic

<400> SEQUENCE: 100

Tyr Cys Ile Gly Tyr
1               5

<210> SEQ ID NO 101
<211> LENGTH: 5
<212> TYPE: PRT
<213> ORGANISM: Artificial Sequence
<220> FEATURE:
<223> OTHER INFORMATION: synthetic

<400> SEQUENCE: 101

Tyr Ile Ile Leu Tyr
1               5

```
<210> SEQ ID NO 102
<211> LENGTH: 5
<212> TYPE: PRT
<213> ORGANISM: Artificial Sequence
<220> FEATURE:
<223> OTHER INFORMATION: synthetic

<400> SEQUENCE: 102

Tyr Phe Ile Pro Tyr
1               5

<210> SEQ ID NO 103
<211> LENGTH: 5
<212> TYPE: PRT
<213> ORGANISM: Artificial Sequence
<220> FEATURE:
<223> OTHER INFORMATION: synthetic

<400> SEQUENCE: 103

Tyr Pro Met Ser Tyr
1               5

<210> SEQ ID NO 104
<211> LENGTH: 5
<212> TYPE: PRT
<213> ORGANISM: Artificial Sequence
<220> FEATURE:
<223> OTHER INFORMATION: synthetic

<400> SEQUENCE: 104

Tyr Pro Pro Ile Tyr
1               5

<210> SEQ ID NO 105
<211> LENGTH: 5
<212> TYPE: PRT
<213> ORGANISM: Artificial Sequence
<220> FEATURE:
<223> OTHER INFORMATION: synthetic

<400> SEQUENCE: 105

Tyr Pro Trp Cys Tyr
1               5

<210> SEQ ID NO 106
<211> LENGTH: 5
<212> TYPE: PRT
<213> ORGANISM: Artificial Sequence
<220> FEATURE:
<223> OTHER INFORMATION: synthetic

<400> SEQUENCE: 106

Tyr Ser Leu Pro Tyr
1               5

<210> SEQ ID NO 107
<211> LENGTH: 5
<212> TYPE: PRT
<213> ORGANISM: Artificial Sequence
<220> FEATURE:
<223> OTHER INFORMATION: synthetic

<400> SEQUENCE: 107

Tyr Thr Val Cys Tyr
1               5
```

```
<210> SEQ ID NO 108
<211> LENGTH: 5
<212> TYPE: PRT
<213> ORGANISM: Artificial Sequence
<220> FEATURE:
<223> OTHER INFORMATION: synthetic

<400> SEQUENCE: 108

Tyr Val Leu Met Tyr
1               5

<210> SEQ ID NO 109
<211> LENGTH: 5
<212> TYPE: PRT
<213> ORGANISM: Artificial Sequence
<220> FEATURE:
<223> OTHER INFORMATION: synthetic

<400> SEQUENCE: 109

Tyr Leu Gly Leu Tyr
1               5

<210> SEQ ID NO 110
<211> LENGTH: 6
<212> TYPE: PRT
<213> ORGANISM: Artificial Sequence
<220> FEATURE:
<223> OTHER INFORMATION: synthetic

<400> SEQUENCE: 110

Tyr Ala Cys Cys Ile Tyr
1               5

<210> SEQ ID NO 111
<211> LENGTH: 5
<212> TYPE: PRT
<213> ORGANISM: Artificial Sequence
<220> FEATURE:
<223> OTHER INFORMATION: synthetic

<400> SEQUENCE: 111

Tyr Gly Met Ser Tyr
1               5

<210> SEQ ID NO 112
<211> LENGTH: 5
<212> TYPE: PRT
<213> ORGANISM: Artificial Sequence
<220> FEATURE:
<223> OTHER INFORMATION: synthetic

<400> SEQUENCE: 112

Tyr Ile Pro Arg Tyr
1               5

<210> SEQ ID NO 113
<211> LENGTH: 5
<212> TYPE: PRT
<213> ORGANISM: Artificial Sequence
<220> FEATURE:
<223> OTHER INFORMATION: synthetic

<400> SEQUENCE: 113

Tyr Thr Pro Met Tyr
1               5

<210> SEQ ID NO 114
```

```
<211> LENGTH: 5
<212> TYPE: PRT
<213> ORGANISM: Artificial Sequence
<220> FEATURE:
<223> OTHER INFORMATION: synthetic

<400> SEQUENCE: 114

Tyr Ala Leu Lys Tyr
1               5

<210> SEQ ID NO 115
<211> LENGTH: 5
<212> TYPE: PRT
<213> ORGANISM: Artificial Sequence
<220> FEATURE:
<223> OTHER INFORMATION: synthetic

<400> SEQUENCE: 115

Tyr Cys Pro Cys Tyr
1               5

<210> SEQ ID NO 116
<211> LENGTH: 5
<212> TYPE: PRT
<213> ORGANISM: Artificial Sequence
<220> FEATURE:
<223> OTHER INFORMATION: synthetic

<400> SEQUENCE: 116

Tyr Ala Ala Thr Tyr
1               5

<210> SEQ ID NO 117
<211> LENGTH: 5
<212> TYPE: PRT
<213> ORGANISM: Artificial Sequence
<220> FEATURE:
<223> OTHER INFORMATION: synthetic

<400> SEQUENCE: 117

Tyr Ala Cys Ile Tyr
1               5

<210> SEQ ID NO 118
<211> LENGTH: 5
<212> TYPE: PRT
<213> ORGANISM: Artificial Sequence
<220> FEATURE:
<223> OTHER INFORMATION: synthetic

<400> SEQUENCE: 118

Tyr Ile Ala Ala Tyr
1               5

<210> SEQ ID NO 119
<211> LENGTH: 5
<212> TYPE: PRT
<213> ORGANISM: Artificial Sequence
<220> FEATURE:
<223> OTHER INFORMATION: synthetic

<400> SEQUENCE: 119

Tyr Ile Cys Val Tyr
1               5

<210> SEQ ID NO 120
<211> LENGTH: 5
```

```
<212> TYPE: PRT
<213> ORGANISM: Artificial Sequence
<220> FEATURE:
<223> OTHER INFORMATION: synthetic

<400> SEQUENCE: 120

Tyr Ile Cys Val Tyr
1               5

<210> SEQ ID NO 121
<211> LENGTH: 5
<212> TYPE: PRT
<213> ORGANISM: Artificial Sequence
<220> FEATURE:
<223> OTHER INFORMATION: synthetic

<400> SEQUENCE: 121

Tyr Ile Trp Gly Tyr
1               5

<210> SEQ ID NO 122
<211> LENGTH: 5
<212> TYPE: PRT
<213> ORGANISM: Artificial Sequence
<220> FEATURE:
<223> OTHER INFORMATION: synthetic

<400> SEQUENCE: 122

Tyr Pro Pro His Tyr
1               5

<210> SEQ ID NO 123
<211> LENGTH: 5
<212> TYPE: PRT
<213> ORGANISM: Artificial Sequence
<220> FEATURE:
<223> OTHER INFORMATION: synthetic

<400> SEQUENCE: 123

Tyr Val Ile Val Tyr
1               5

<210> SEQ ID NO 124
<211> LENGTH: 5
<212> TYPE: PRT
<213> ORGANISM: Artificial Sequence
<220> FEATURE:
<223> OTHER INFORMATION: synthetic

<400> SEQUENCE: 124

Tyr Gly Phe Cys Tyr
1               5

<210> SEQ ID NO 125
<211> LENGTH: 5
<212> TYPE: PRT
<213> ORGANISM: Artificial Sequence
<220> FEATURE:
<223> OTHER INFORMATION: synthetic

<400> SEQUENCE: 125

Tyr Trp Met Pro Tyr
1               5

<210> SEQ ID NO 126
<211> LENGTH: 5
<212> TYPE: PRT
```

```
<213> ORGANISM: Artificial Sequence
<220> FEATURE:
<223> OTHER INFORMATION: synthetic

<400> SEQUENCE: 126

Tyr Gly Phe Pro Tyr
1               5

<210> SEQ ID NO 127
<211> LENGTH: 5
<212> TYPE: PRT
<213> ORGANISM: Artificial Sequence
<220> FEATURE:
<223> OTHER INFORMATION: synthetic

<400> SEQUENCE: 127

Tyr Leu Trp Val Tyr
1               5

<210> SEQ ID NO 128
<211> LENGTH: 5
<212> TYPE: PRT
<213> ORGANISM: Artificial Sequence
<220> FEATURE:
<223> OTHER INFORMATION: synthetic

<400> SEQUENCE: 128

Tyr Met Leu Pro Tyr
1               5

<210> SEQ ID NO 129
<211> LENGTH: 5
<212> TYPE: PRT
<213> ORGANISM: Artificial Sequence
<220> FEATURE:
<223> OTHER INFORMATION: synthetic

<400> SEQUENCE: 129

Tyr Met Pro Ile Tyr
1               5

<210> SEQ ID NO 130
<211> LENGTH: 5
<212> TYPE: PRT
<213> ORGANISM: Artificial Sequence
<220> FEATURE:
<223> OTHER INFORMATION: synthetic

<400> SEQUENCE: 130

Tyr Ser Val Ile Tyr
1               5

<210> SEQ ID NO 131
<211> LENGTH: 5
<212> TYPE: PRT
<213> ORGANISM: Artificial Sequence
<220> FEATURE:
<223> OTHER INFORMATION: synthetic

<400> SEQUENCE: 131

Tyr Pro Ala His Tyr
1               5

<210> SEQ ID NO 132
<211> LENGTH: 5
<212> TYPE: PRT
<213> ORGANISM: Artificial Sequence
```

```
<220> FEATURE:
<223> OTHER INFORMATION: synthetic

<400> SEQUENCE: 132

Tyr Ala Met Thr Tyr
1               5

<210> SEQ ID NO 133
<211> LENGTH: 5
<212> TYPE: PRT
<213> ORGANISM: Artificial Sequence
<220> FEATURE:
<223> OTHER INFORMATION: synthetic

<400> SEQUENCE: 133

Tyr Ile Leu Leu Tyr
1               5

<210> SEQ ID NO 134
<211> LENGTH: 5
<212> TYPE: PRT
<213> ORGANISM: Artificial Sequence
<220> FEATURE:
<223> OTHER INFORMATION: synthetic

<400> SEQUENCE: 134

Tyr Gly Pro Trp Tyr
1               5

<210> SEQ ID NO 135
<211> LENGTH: 5
<212> TYPE: PRT
<213> ORGANISM: Artificial Sequence
<220> FEATURE:
<223> OTHER INFORMATION: synthetic

<400> SEQUENCE: 135

Tyr Gly Pro Ser Tyr
1               5

<210> SEQ ID NO 136
<211> LENGTH: 5
<212> TYPE: PRT
<213> ORGANISM: Artificial Sequence
<220> FEATURE:
<223> OTHER INFORMATION: synthetic

<400> SEQUENCE: 136

Tyr Ile Pro Ser Tyr
1               5

<210> SEQ ID NO 137
<211> LENGTH: 5
<212> TYPE: PRT
<213> ORGANISM: Artificial Sequence
<220> FEATURE:
<223> OTHER INFORMATION: synthetic

<400> SEQUENCE: 137

Tyr Thr Leu Cys Tyr
1               5

<210> SEQ ID NO 138
<211> LENGTH: 5
<212> TYPE: PRT
<213> ORGANISM: Artificial Sequence
<220> FEATURE:
```

```
<223> OTHER INFORMATION: synthetic

<400> SEQUENCE: 138

Tyr Ala His Ile Tyr
1               5

<210> SEQ ID NO 139
<211> LENGTH: 5
<212> TYPE: PRT
<213> ORGANISM: Artificial Sequence
<220> FEATURE:
<223> OTHER INFORMATION: synthetic

<400> SEQUENCE: 139

Tyr Ala His Tyr Tyr
1               5

<210> SEQ ID NO 140
<211> LENGTH: 5
<212> TYPE: PRT
<213> ORGANISM: Artificial Sequence
<220> FEATURE:
<223> OTHER INFORMATION: synthetic

<400> SEQUENCE: 140

Tyr Ala Pro Ser Tyr
1               5

<210> SEQ ID NO 141
<211> LENGTH: 5
<212> TYPE: PRT
<213> ORGANISM: Artificial Sequence
<220> FEATURE:
<223> OTHER INFORMATION: synthetic

<400> SEQUENCE: 141

Tyr Ala Trp Cys Tyr
1               5

<210> SEQ ID NO 142
<211> LENGTH: 5
<212> TYPE: PRT
<213> ORGANISM: Artificial Sequence
<220> FEATURE:
<223> OTHER INFORMATION: synthetic

<400> SEQUENCE: 142

Tyr Gln Pro Ser Tyr
1               5

<210> SEQ ID NO 143
<211> LENGTH: 5
<212> TYPE: PRT
<213> ORGANISM: Artificial Sequence
<220> FEATURE:
<223> OTHER INFORMATION: synthetic

<400> SEQUENCE: 143

Tyr Ile Phe Lys Tyr
1               5

<210> SEQ ID NO 144
<211> LENGTH: 5
<212> TYPE: PRT
<213> ORGANISM: Artificial Sequence
<220> FEATURE:
<223> OTHER INFORMATION: synthetic
```

```
<400> SEQUENCE: 144

Tyr Ile Pro Asn Tyr
1               5

<210> SEQ ID NO 145
<211> LENGTH: 5
<212> TYPE: PRT
<213> ORGANISM: Artificial Sequence
<220> FEATURE:
<223> OTHER INFORMATION: synthetic

<400> SEQUENCE: 145

Tyr Phe Pro Ile Tyr
1               5

<210> SEQ ID NO 146
<211> LENGTH: 5
<212> TYPE: PRT
<213> ORGANISM: Artificial Sequence
<220> FEATURE:
<223> OTHER INFORMATION: synthetic

<400> SEQUENCE: 146

Tyr Pro Ser Thr Tyr
1               5

<210> SEQ ID NO 147
<211> LENGTH: 5
<212> TYPE: PRT
<213> ORGANISM: Artificial Sequence
<220> FEATURE:
<223> OTHER INFORMATION: synthetic

<400> SEQUENCE: 147

Tyr Pro Thr Trp Tyr
1               5

<210> SEQ ID NO 148
<211> LENGTH: 5
<212> TYPE: PRT
<213> ORGANISM: Artificial Sequence
<220> FEATURE:
<223> OTHER INFORMATION: synthetic

<400> SEQUENCE: 148

Tyr Pro Trp Phe Tyr
1               5

<210> SEQ ID NO 149
<211> LENGTH: 5
<212> TYPE: PRT
<213> ORGANISM: Artificial Sequence
<220> FEATURE:
<223> OTHER INFORMATION: synthetic

<400> SEQUENCE: 149

Tyr Thr Met Leu Tyr
1               5

<210> SEQ ID NO 150
<211> LENGTH: 5
<212> TYPE: PRT
<213> ORGANISM: Artificial Sequence
<220> FEATURE:
<223> OTHER INFORMATION: synthetic
```

```
<400> SEQUENCE: 150

Tyr Ala Trp Ile Tyr
1               5

<210> SEQ ID NO 151
<211> LENGTH: 5
<212> TYPE: PRT
<213> ORGANISM: Artificial Sequence
<220> FEATURE:
<223> OTHER INFORMATION: synthetic

<400> SEQUENCE: 151

Tyr Cys Gly Phe Tyr
1               5

<210> SEQ ID NO 152
<211> LENGTH: 5
<212> TYPE: PRT
<213> ORGANISM: Artificial Sequence
<220> FEATURE:
<223> OTHER INFORMATION: synthetic

<400> SEQUENCE: 152

Tyr Cys His Thr Tyr
1               5

<210> SEQ ID NO 153
<211> LENGTH: 5
<212> TYPE: PRT
<213> ORGANISM: Artificial Sequence
<220> FEATURE:
<223> OTHER INFORMATION: synthetic

<400> SEQUENCE: 153

Tyr Gly Thr Trp Tyr
1               5

<210> SEQ ID NO 154
<211> LENGTH: 5
<212> TYPE: PRT
<213> ORGANISM: Artificial Sequence
<220> FEATURE:
<223> OTHER INFORMATION: synthetic

<400> SEQUENCE: 154

Tyr Ile Leu Trp Tyr
1               5

<210> SEQ ID NO 155
<211> LENGTH: 5
<212> TYPE: PRT
<213> ORGANISM: Artificial Sequence
<220> FEATURE:
<223> OTHER INFORMATION: synthetic

<400> SEQUENCE: 155

Tyr Gly Trp Thr Tyr
1               5

<210> SEQ ID NO 156
<211> LENGTH: 5
<212> TYPE: PRT
<213> ORGANISM: Artificial Sequence
<220> FEATURE:
<223> OTHER INFORMATION: synthetic

<400> SEQUENCE: 156
```

```
Tyr Ile Phe Cys Tyr
1               5

<210> SEQ ID NO 157
<211> LENGTH: 5
<212> TYPE: PRT
<213> ORGANISM: Artificial Sequence
<220> FEATURE:
<223> OTHER INFORMATION: synthetic

<400> SEQUENCE: 157

Tyr Arg Thr Thr Tyr
1               5

<210> SEQ ID NO 158
<211> LENGTH: 5
<212> TYPE: PRT
<213> ORGANISM: Artificial Sequence
<220> FEATURE:
<223> OTHER INFORMATION: synthetic

<400> SEQUENCE: 158

Tyr Gln Pro Met Tyr
1               5

<210> SEQ ID NO 159
<211> LENGTH: 5
<212> TYPE: PRT
<213> ORGANISM: Artificial Sequence
<220> FEATURE:
<223> OTHER INFORMATION: synthetic

<400> SEQUENCE: 159

Tyr Ile Lys Tyr Tyr
1               5

<210> SEQ ID NO 160
<211> LENGTH: 5
<212> TYPE: PRT
<213> ORGANISM: Artificial Sequence
<220> FEATURE:
<223> OTHER INFORMATION: synthetic

<400> SEQUENCE: 160

Tyr Val Leu Tyr Tyr
1               5
```